United States Patent
Lin et al.

(10) Patent No.: US 6,815,206 B2
(45) Date of Patent: *Nov. 9, 2004

(54) CONTAINER MONITORING SYSTEM

(75) Inventors: Szu-Min Lin, Laguna Hills, CA (US); Su-Syin Wu, Irvine, CA (US)

(73) Assignee: Ethicon, Inc., Somerville, NJ (US)

( * ) Notice: Subject to any disclaimer, the term of this patent is extended or adjusted under 35 U.S.C. 154(b) by 14 days.

This patent is subject to a terminal disclaimer.

(21) Appl. No.: 09/742,315

(22) Filed: Dec. 21, 2000

(65) Prior Publication Data

US 2002/0022246 A1 Feb. 21, 2002

Related U.S. Application Data

(63) Continuation-in-part of application No. 09/172,360, filed on Oct. 14, 1998, now Pat. No. 6,193,931, which is a continuation-in-part of application No. 08/934,496, filed on Sep. 19, 1997, now Pat. No. 5,834,313.

(51) Int. Cl.[7] .......................... G01N 31/00; G01N 33/00
(52) U.S. Cl. ............................. 436/1; 436/126; 422/28; 422/34; 422/36; 422/37
(58) Field of Search .............................. 422/28, 34, 36, 422/37, 300; 436/1, 126, 128

(56) References Cited

U.S. PATENT DOCUMENTS

| | | |
|---|---|---|
| 3,371,985 A | 3/1968 | Wyka |
| 3,960,670 A | 6/1976 | Pflug |
| 4,169,123 A | 9/1979 | Moore et al. |
| 4,169,124 A | 9/1979 | Forstrom et al. |
| 4,230,663 A | 10/1980 | Forstrom et al. |
| 4,410,492 A | 10/1983 | Kaye |
| 4,580,682 A | 4/1986 | Gorski et al. |
| 4,636,472 A * | 1/1987 | Bruso ...................... 435/287.4 |
| 4,643,876 A | 2/1987 | Jacobs et al. |
| 4,710,233 A | 12/1987 | Hohmann et al. |
| 4,710,350 A | 12/1987 | Petersen |
| 4,756,882 A | 7/1988 | Jacobs et al. |
| 4,877,963 A | 10/1989 | Min-Jenn |
| 4,909,999 A | 3/1990 | Cummings et al. |
| 4,943,414 A | 7/1990 | Jacobs et al. |
| 4,952,370 A | 8/1990 | Cummings et al. |
| 4,956,145 A | 9/1990 | Cummings et al. |
| 5,069,880 A | 12/1991 | Karlson |
| 5,073,488 A | 12/1991 | Matner et al. |
| 5,074,200 A | 12/1991 | Ruozi |
| 5,087,418 A | 2/1992 | Jacob |
| 5,115,166 A | 5/1992 | Campbell et al. |

(List continued on next page.)

FOREIGN PATENT DOCUMENTS

| | | |
|---|---|---|
| CA | 2149923 A1 | 6/1994 |
| DE | 2823917 A1 | 12/1977 |
| DE | 4102055 A1 | 8/1991 |
| EP | 223479 A2 | 5/1987 |
| EP | 302419 A2 | 2/1989 |
| EP | 207417 B1 | 9/1990 |
| EP | 456135 A2 | 11/1991 |
| EP | 898971 A | 3/1999 |
| EP | 923949 A | 6/1999 |

OTHER PUBLICATIONS

Abe M. H., et al; English Abstract for German Patent DE 4102055A1; Aug. 1, 1999; Dialog File No. 351; Accession No. 8727436; Derwent World Patents Index; 2004.

Edel H. H.; English Abstract for German Patent DE 2623917; Dec. 15, 1977; Dialog File No. 351; Accession No. 1869266; Derwent World Patents Index; 2004.

*Primary Examiner*—Jill Warden
*Assistant Examiner*—LaToya Cross

(57) ABSTRACT

A sterilization system uses a sterilization process monitoring device which is capable of indicating the efficacy of the sterilization process. To enhance accuracy of the monitoring function, the monitoring device is located in such a fashion that an antimicrobial agent used in the process can only reach the monitor through an area containing the article to be sterilized.

22 Claims, 23 Drawing Sheets

U.S. PATENT DOCUMENTS

| | | | |
|---|---|---|---|
| 5,160,700 A | 11/1992 | Anderson et al. | |
| 5,217,901 A | * 6/1993 | Dyckman | 435/287.4 |
| 5,225,160 A | 7/1993 | Sanford et al. | |
| 5,252,304 A | 10/1993 | Miyoshi | |
| 5,286,448 A | 2/1994 | Childers | |
| 5,310,524 A | 5/1994 | Campbell et al. | |
| 5,344,622 A | 9/1994 | Faddis et al. | |
| 5,346,075 A | 9/1994 | Nichols et al. | |
| 5,413,760 A | 5/1995 | Campbell et al. | |
| 5,443,801 A | 8/1995 | Langford | |
| 5,451,368 A | 9/1995 | Jacob | |
| 5,486,459 A | 1/1996 | Burnham et al. | |
| 5,487,877 A | 1/1996 | Choi | |
| 5,492,672 A | 2/1996 | Childers et al. | |
| 5,527,508 A | 6/1996 | Childers et al. | |
| 5,534,221 A | 7/1996 | Hillebrenner et al. | |
| 5,552,320 A | 9/1996 | Smith | |
| 5,556,607 A | 9/1996 | Childers et al. | |
| 5,580,530 A | 12/1996 | Kowatsch et al. | |
| 5,633,424 A | 5/1997 | Graves et al. | |
| 5,656,238 A | 8/1997 | Spencer et al. | |
| 5,667,753 A | 9/1997 | Jacobs et al. | |
| 5,770,739 A | 6/1998 | Lin et al. | |
| 5,792,422 A | 8/1998 | Lin et al. | |
| 5,834,313 A | 11/1998 | Lin | |
| 6,013,227 A | 1/2000 | Lin et al. | |
| 6,015,529 A | 1/2000 | Lin et al. | |
| 6,066,294 A | 5/2000 | Lin et al. | |
| 6,193,931 B1 | 2/2001 | Lin et al. | |
| 6,224,828 B1 | 5/2001 | Lin et al. | |

\* cited by examiner

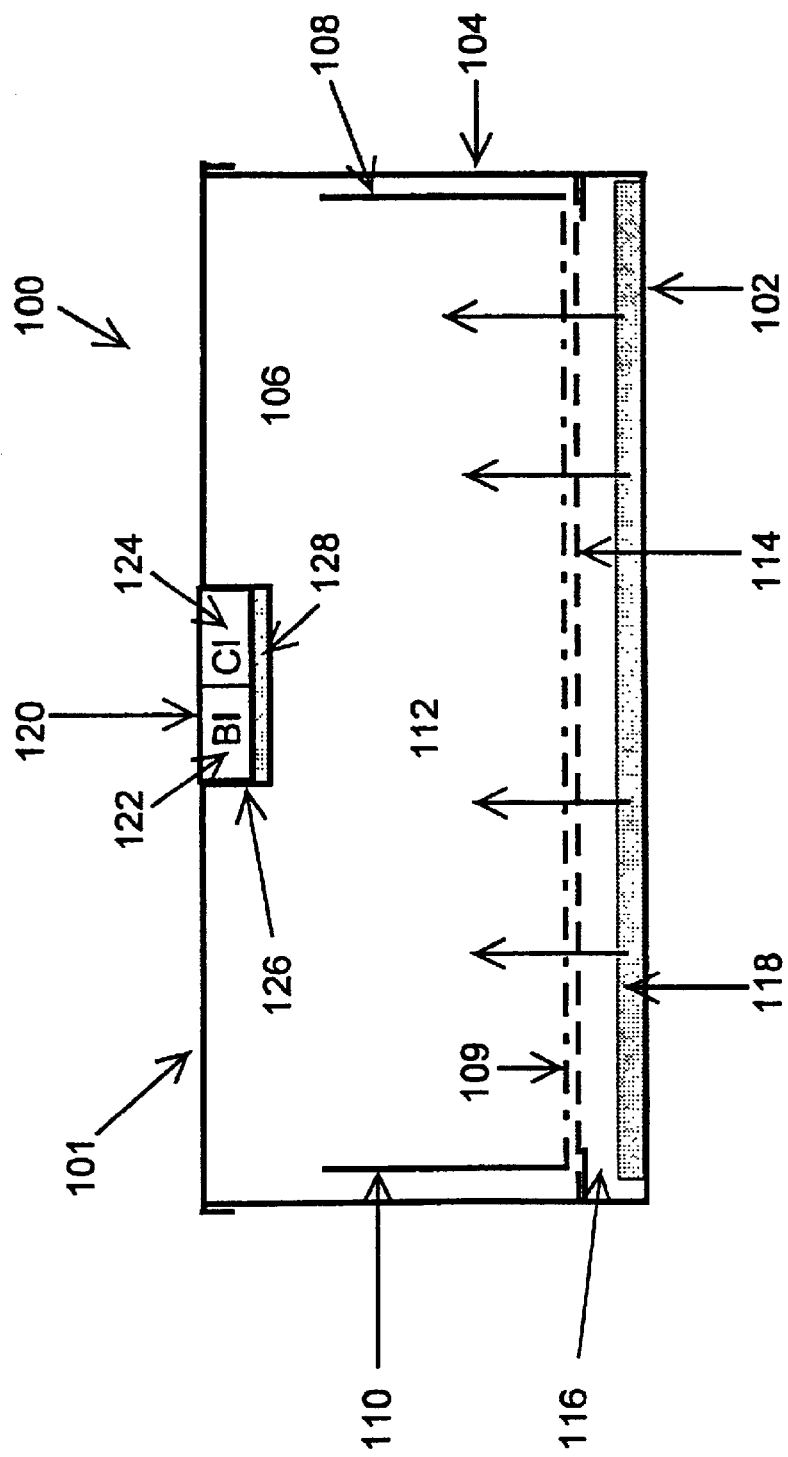

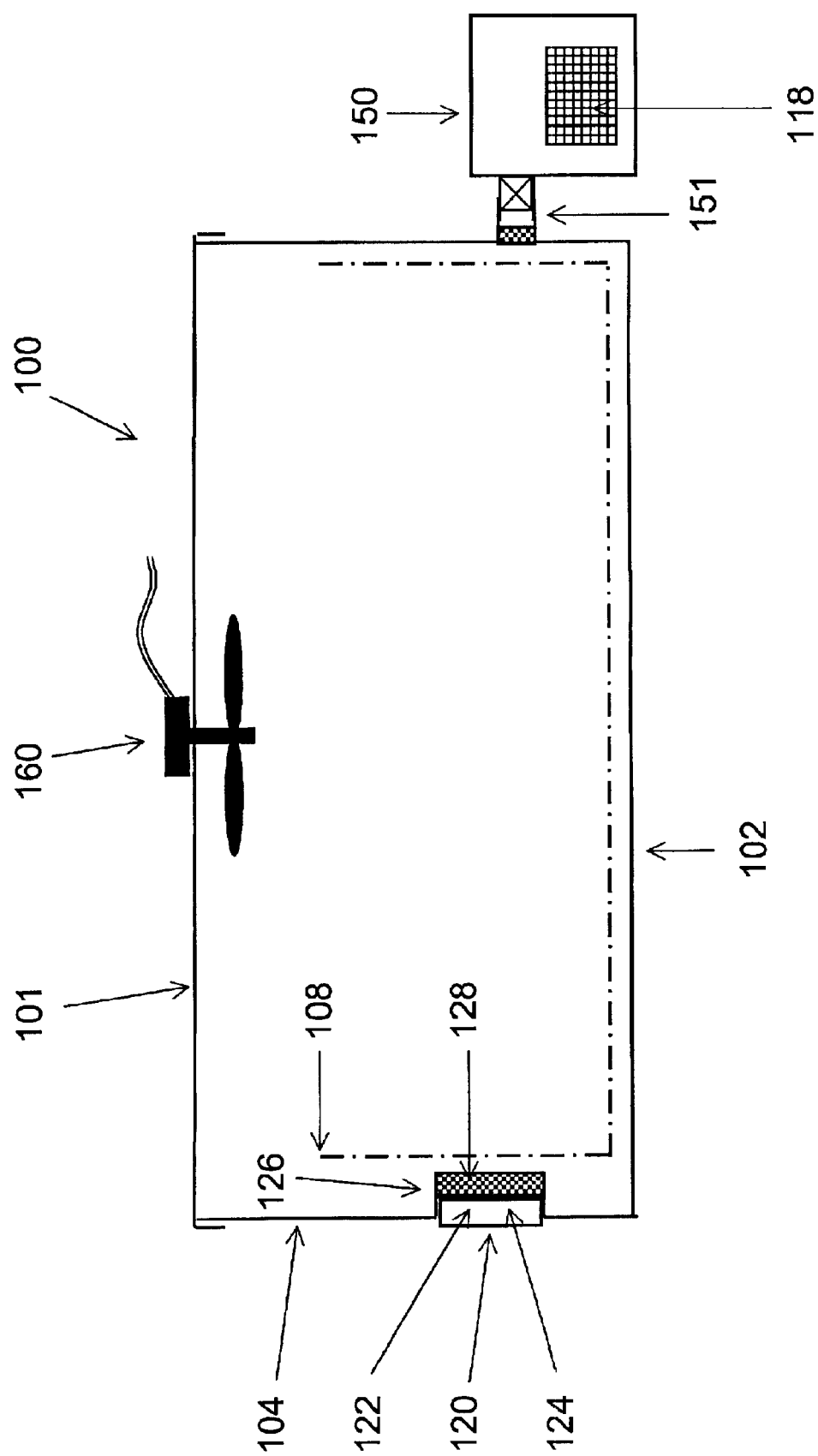

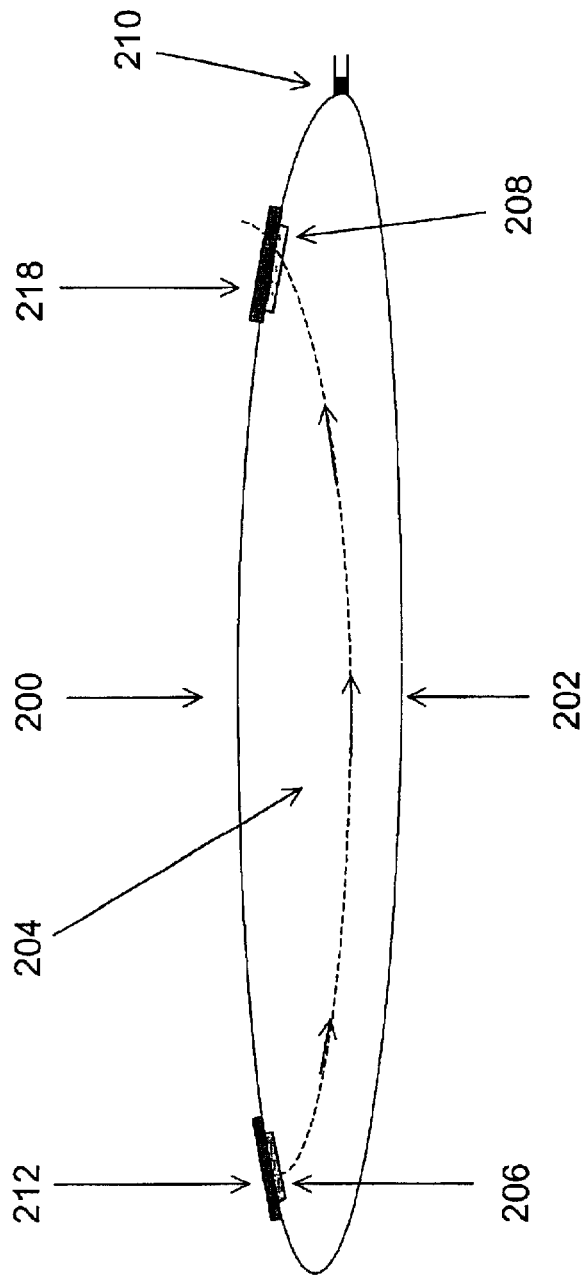
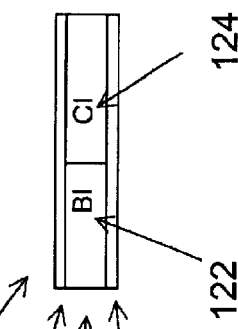
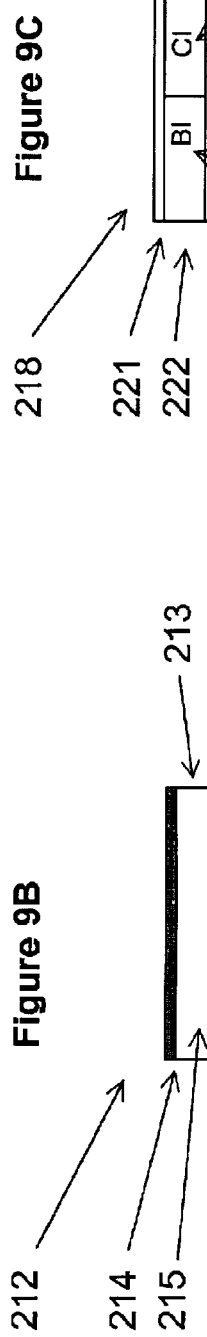
Figure 9A
Figure 9B
Figure 9C

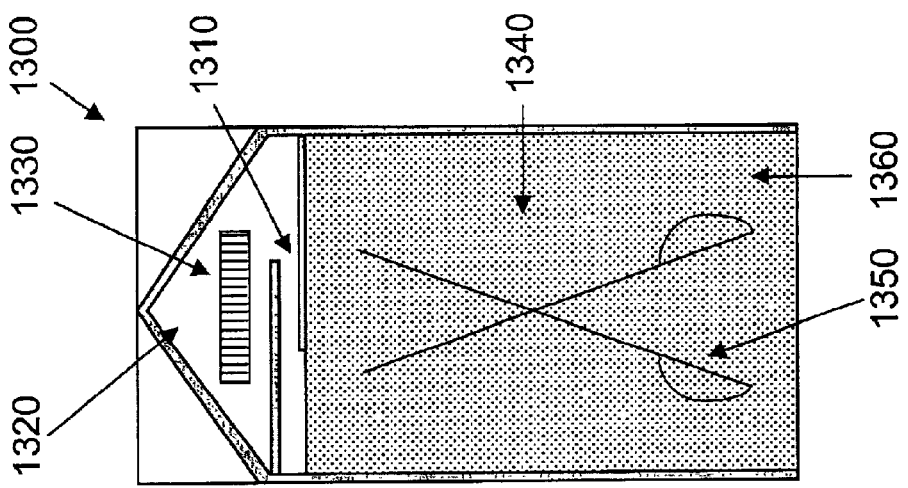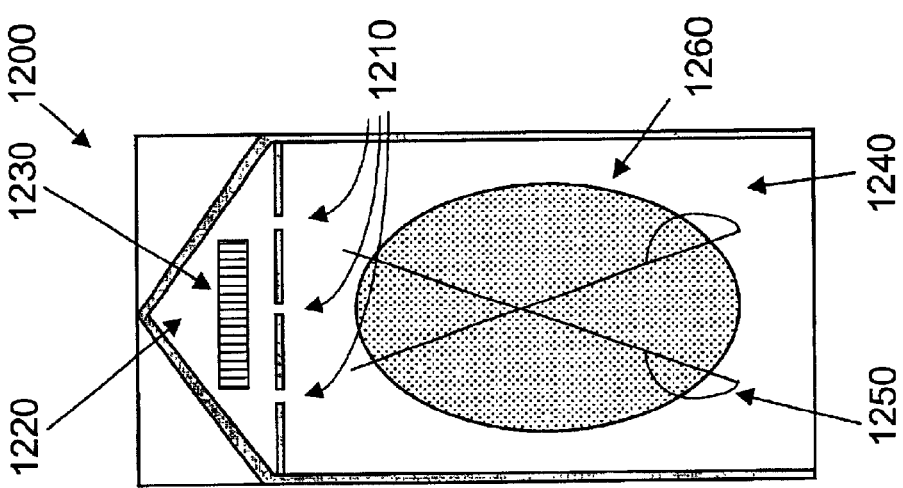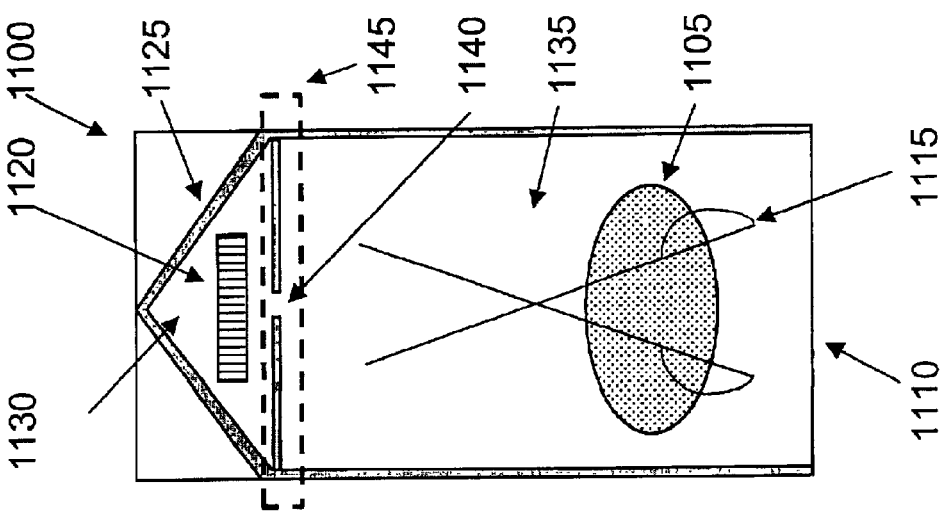

CONTAINER MONITORING SYSTEM

PRIORITIES CLAIMED

This application is a continuation-in-part of U.S. patent application Ser. No. 09/172,360 filed Oct. 14, 1998, now U.S. Pat. No. 6,193,931, which is a continuation-in-part of U.S. patent application Ser. No. 08/934,496 filed Sep. 19, 1997, now U.S. Pat. No. 5,834,313.

BACKGROUND OF THE INVENTION

1. Field of the Invention

The present invention generally relates to sterilization processes, and more particularly, to the techniques for monitoring the efficacy of a container or a pouch system.

2. Description of the Related Art

A sterilization process generally involves in exposing the articles to be sterilized to a sterilizing medium that can kill bacterial microorganisms. Such processes are performed in sterilization chambers. The articles to be sterilized are often delivered to the sterilization chambers within a sterilization container in which the articles are both sterilized and subsequently stored in their sterilized state. In some instances, articles are merely disinfected, but are often nevertheless delivered within a container.

The containers are generally permeable to a sterilizing medium so that the sterilizing medium may enter the container during the sterilization process. A sterilizing medium may be a sterilant gas or vapor (e.g., hydrogen peroxide vapor) released by a sterilant source which is placed into or delivered into the sterilization container. As used hereinafter, the terms "gas" and "vapor" are used interchangeably. Such gas permeable containers may, for example, include pouches made of gas permeable materials or rigid trays wrapped with gas permeable wraps. In fact, a sterilization container may be configured as a sealable rigid container having ports to deliver a sterilant after the container has been sealed. In all above examples, however, the sterilization containers prevent the entry of the microorganisms into the container and thereby maintain the sterilized state of the articles therein.

In modern medical and dental practice, it is important to monitor the efficacy of the sterilization processes. That is, at the end of the sterilization cycle, it must be verified that all of the articles have been adequately exposed to the sterilizing medium and the existing microorganisms have been killed. Conventional sterilization processes commonly have two underlying monitoring devices that address such concerns, namely, biological indicators and chemical indicators. A biological indicator (BI) is a type of device having a source of microorganisms. In this context, the source of microorganisms refers to a predetermined concentration and type of microorganisms which are generally impregnated into coated onto a substrate, such as paper, fiberglass, or stainless steel. A biological indicator is used to monitor the sterilization process and determine whether the particular sterilant succeeded in killing or inactivating all the microorganisms in the load to be sterilized. In practice, the biological indicator is maintained in a package which is made of gas permeable materials. During the sterilization process, the biological indicators are conventionally placed outside the sterilization containers so that the biological indicator can be retrieved without compromising the sterility of the devices within the container. After exposure to the sterilization process, the source of microorganisms is placed in a sterile culture medium and incubated for a predetermined period of time. Any surviving microorganisms or growth of microorganisms indicates the incompleteness of the sterilization process in the container. One example of such a BI is shown in the Smith, U.S. Pat. No. 5,552,320, issued Sep. 3, 1996, incorporated herein by reference. Alternatively, a source of enzymes which mimic the response of living organisms to the sterilization procedure in a measurable fashion may be substituted for living microorganisms. Examples of this type of BI are shown in the Matner, U.S. Pat. No. 5,073,488 issued Dec. 17, 1991 and the Burnham, U.S. Pat. No. 5,486,459, issued Jan. 23, 1996, each of which are incorporated herein by reference.

On the other hand, chemical indicators (CI) are devices that primarily indicates whether or not the sterilization process cycle is carried out properly to deliver the sterilant to the sterilization chamber. Thus, chemical indicators do not necessarily provide a true indication that sterility has been achieved. Chemical indicators contain specific chemical compositions which chemically reacts and change color or other configurations when exposed to the sterilizing medium. Additionally, chemical indicators may be designed to include and respond to a plurality of sterilization process parameters. For example, depending on the classification of the chemicals indicator, a chemical indicator can be designed to indicate or respond to certain sterilant concentrations, humidity, time, temperature, sterilant's pH or pressure.

During conventional sterilization processes, biological and chemical indicators are typically placed outside the gas permeable sterilization containers in which the load of the articles to be sterilized are placed. Upon completion of the sterilization process, containers, which are in their sealed state and with a presumably sterilized load, are often stored for a period of time before the sterilized articles are needed. In such conventional processes, the actual state of the sterilization inside the container is determined by inspecting the indicators located outside the container to determine whether the sterilization has been achieved. However, in practice, this approach has serious drawbacks because these indicators cannot provide accurate information about the sterilization status of the articles in the container. Since the indicators only display the outside readings, there is no way of knowing whether sterilization has been achieved inside the container.

An alternative approach utilizes two chemical indicators to overcome the above given drawback. In this approach one of the chemical indicators is placed into the container adjacent to the load of articles. Unfortunately, the problem with this approach is that the actual state of the sterilization can only be determined by opening the container and inspecting the chemical indicator placed inside the container. However, this is also not practical and disturbs the sealed state of the container and the sterility of the devices therein. There also is a possibility that sterilization conditions were not achieved inside the container. Accordingly, throughout the storage period, the actual state of the sterilization process cannot be known.

Some container systems have a clear barrier through which a chemical indicator, but not a biological indicator, can be read. However, such chemical indicators cannot be removed without breaking the barrier. Moreover, in such a system, the chemical indicator is included within the load, so it is exposed to sterilant at the same time as the load. As a result, the chemical indicator may indicate a sterile result, even when portions of the load have not been exposed to sufficient sterilant to achieve sterility.

In view of the foregoing, there is a need for a new monitoring system for sterilization processes which is capable of indicating the state of the sterilization in an enclosed sterilization container while maintaining the sealed state of the sterilization container.

SUMMARY OF THE INVENTION

A system, according to the present invention, for monitoring a sterilization or disinfection process comprises a container defining a first space and a second space which are in fluid communication with each other. The first space is adapted to contain one or more articles to be sterilized or disinfected and the second space contains therein at least one indicator for indicating a parameter relevant to the sterilization or disinfection process. An antimicrobial source provides an antimicrobial agent to the first space. The second area is in fluid communication with the antimicrobial source only through the first space.

The antimicrobial source can comprise an aperture into the first space from outside of the container whereby antimicrobial fluids in an area around the container may diffuse into the first space through the aperture. Alternatively, the antimicrobial source can comprise a supply of antimicrobial fluid within the first space. Preferably, the antimicrobial fluid comprises hydrogen peroxide, and more preferably hydrogen peroxide vapor.

Preferably, the container is impermeable to microorganisms. A flow restriction can be provided between the first space and the second space. The second space may be detachable from the first space.

In one aspect of the invention, the container comprises a pouch.

The he indicator preferably comprises a biological indicator or a chemical indicator. When the container comprises a pouch, one convenient option is to print the chemical indicator on the pouch inside the second space.

In another aspect of the invention, the first space is divided into two or more subspaces connected in series between the source of antimicrobial fluid and the second space. One, more, or all of these subspaces, in addition to the second space can be made so as to be detachable from each other. A fan can be provided to assist flow through the container from the source of antimicrobial fluid to the second space.

A method, according to the present invention, for monitoring a disinfection or sterilization procedure comprises providing a container or pouch impermeable to microorganisms having a first space and a second space in fluid communication with each other. An article to be disinfected or sterilized is placed into the first area and an indicator is placed into the second area. An antimicrobial agent is provided in the first space and flowed to the second area only from the first area. A relevant function of the disinfection or sterilization procedure is read with the indicator.

The antimicrobial agent can be recirculated back to the first space from the second space.

When the container is a pouch the first space can be sealed from the second space after flowing the antimicrobial agent into the second space and then the indicator can be removed from the second space. The sealing can be accomplished by heat sealing a portion of the pouch between the first space and the second space.

BRIEF DESCRIPTION OF THE DRAWINGS

FIG. 1A is a schematic view of a system comprising a sterilization container with an attachable process monitoring device;

FIG. 1B is a schematic detail view of the attachable process monitoring device;

FIG. 8 is a schematic view of an eighth embodiment of the system wherein the separate sterilant enclosure and the process monitor device are placed over the opposite sides of the sterilization container;

FIG. 9A is a schematic view of an alternative embodiment of the system comprising a flexible container with an attachable process monitor device and an attachable sterilant source cartridge;

FIG. 9B is a schematic view of the attachable sterilant source cartridge;

FIG. 9C is a schematic view of the attachable process monitor device;

FIG. 19 is a schematic view of a pouch having a gas or vapor permeable window and a partition to separate the indicator and the article to be processed;

FIG. 20 is a schematic view of a pouch with a partition having multiple openings between the area for the indicator and the area for the article to be processed;

FIG. 21 is a schematic view of a pouch with a communication path formed with two partially overlapped partitions;

DETAILED DESCRIPTION OF THE PREFERRED EMBODIMENT

Figure 1C:
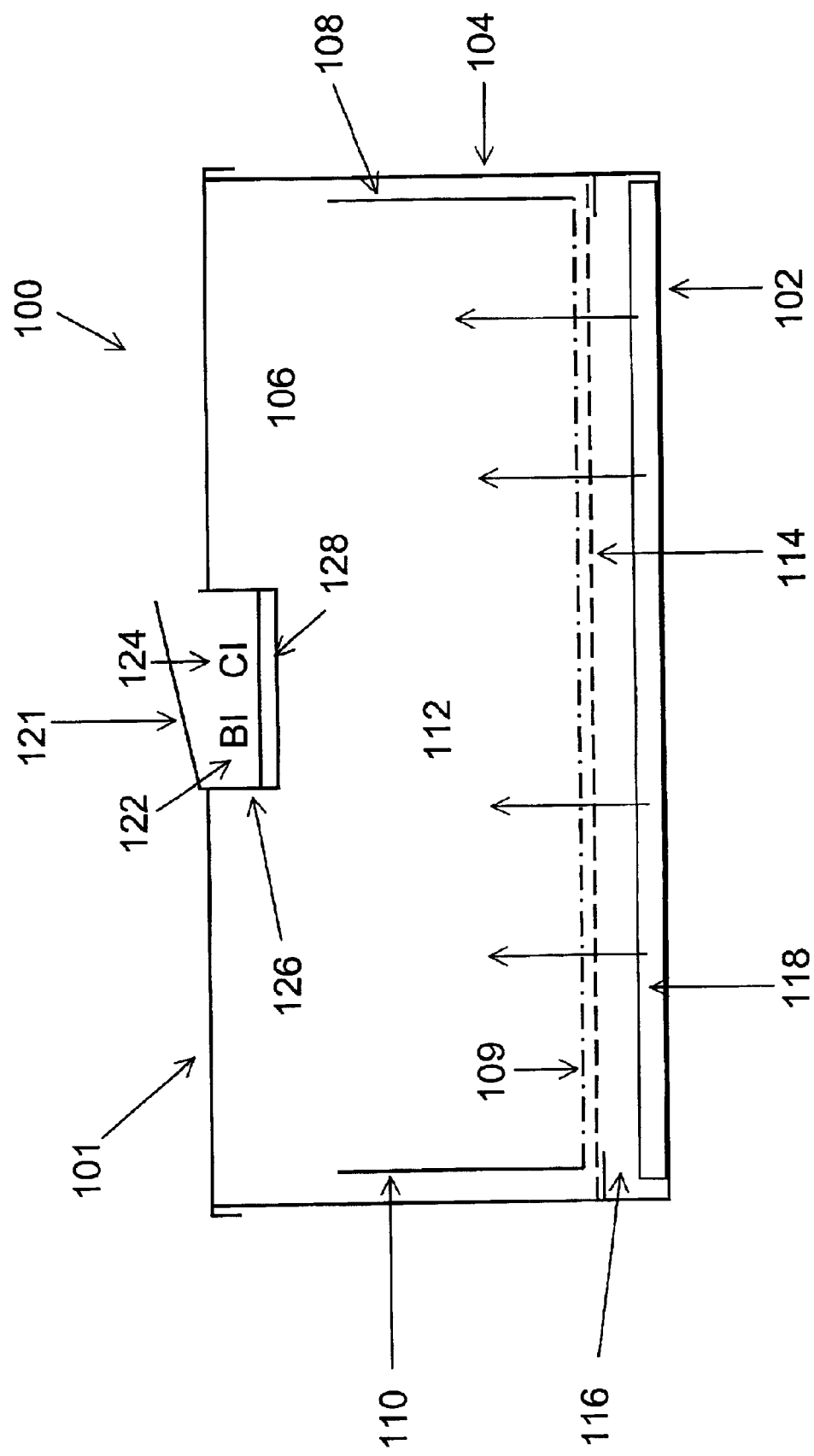
FIG. 1C is a schematic view of a modified form of the first embodiment of the system in which a process monitoring device is provided within an openable housing.

As an improvement to conventional monitoring systems for sterilization processes, the process of the preferred embodiments are preferably capable of indicating the efficacy of the sterilization process in an enclosed sterilization container while still maintaining the sealed state of the sterilization container. Reference will now be made to the drawings wherein like numerals refer to like parts throughout.

As illustrated in FIG. 1, sterilization system of the preferred embodiment comprises a first container 100. In the preferred embodiment, the first container 100 is preferably a rigid enclosed container comprising a top portion 101, a bottom portion 102 and a peripheral wall 104 which is preferably perpendicularly attached to the periphery of the bottom portion 102.

Preferred materials for manufacturing the solid container 100 may be metals or polymers such as aluminum, stainless steel or plastics. The bottom portion 102 and the peripheral wall 104 define a container housing 106. The container housing 106 may be preferably configured and dimensioned to receive at least one optional second container 108. The second container 108 may be configured as a tray having a perforated bottom 109 and a peripheral wall 110. The perforated bottom 109 and the peripheral wall 110 of the tray 108 define a second housing 112 to accommodate articles (not shown) to be sterilized. Inside the container housing 106, the tray 108 may be removably placed on an optional rack 114 which may be made of a perforated plate. Preferably, the rack 114 is removably attached to the inside of peripheral wall 104 so as to stay elevated from the bottom portion 102 of the container and so as to define a sterilant housing 116. A sterilant source 118 may be further placed into the sterilant housing 116 to produce a sterilizing medium such as a vapor sterilant. An exemplary sterilant source may be liquid hydrogen peroxide, solid hydrogen peroxide complex and peracetic acid. A variety of solid peroxide complexes are described in allowed U.S. patent application Ser. No. 08/549,425, filed Oct. 27, 1995, the complete disclosure of which is hereby incorporated by this reference thereto. The top portion 101 of the container 100 comprises a removable container lid which seals the container housing 106 when closed.

As illustrated in FIGS. 1A–1B, in the preferred embodiment, a cartridge 120 comprising at least one process monitor device may be removably positioned onto the lid 101 of the container 100. In accordance with the principles of the present invention, these process monitor devices may comprise at least one biological indicator 122 and/or at least one chemical indicator 124. Either or both of these indicators can be provided with a unique identifier, such as a serial number, which pairs the indicator with the container. Thus, the container can be provided with the same identifier in order to pair it with the indicator.

As previously noted in the background section, the biological indicator 122 is kept in a gas permeable pack which permit the passage of the sterilizing gas but not the passage of microorganisms. In the preferred embodiment, such packs may, for example, be made of spun-bond polyethylene (e.g. Tyvek™) or non-woven polypropylene wrap (e.g. CSR-wrap) materials. The cartridge 120 containing the biological and the chemical indicators 122 and 124 may be placed into a cartridge holder 126. The bottom layer of the cartridge 120 can optionally comprise a gas permeable material. The cartridge holder 126 may be configured to have a recessed cavity having a bottom 128 portion and downwardly extending into the container housing 106. The cartridge holder 126 may be dimensioned to receive at least one cartridge 120. In the preferred embodiment, the bottom portion 128 of the cartridge holder 126 is made of above-mentioned gas permeable and microorganism impermeable materials (e.g., Tyvek™ or CSR-wrap) so that the sterilant vapor from the housing 106 can pass through the gas permeable material and reach indicators 122 and 124. The gas or vapor permeable and microorganism impermeable material can be heat sealed on the bottom portion 128. The cartridge 120 may be secured in cartridge holder 126 by employing a number of fastening mechanisms such as snap-on type connectors or the like. However, with possible modifications in the cartridge 120 and the cartridge holder 126, the cartridge 120 may be secured to the holder 126 by a twist or a screw type of connector as well.

In the process of the preferred embodiment, the vapor sterilant such as hydrogen peroxide vapor diffuses through the rack 114 and the perforated bottom 109 of the tray 108 (in the direction of the arrows) and thereby contacting the articles and filling the container housing 106. While the sterilization process progresses, the sterilant vapor also diffuses through the gas permeable membrane 128 and subsequently into the cartridge 120 having the biological and/or chemical indicators 122 and 124. The sterilant vapor entering the cartridge 120 exposes indicators to the same sterilizing environment encountered by the articles in the tray 108. At this point, it is highly desirable that, on the container 100, the gas permeable membrane 128 of the holder 126 be accommodated at a farthest possible location from the sterilant source 118. As a result of this, the articles in the container 100 are treated with the sterilant vapor before the sterilant vapor diffuses through the gas permeable membrane 128. Since the indicators 122 and 124 are the last place for sterilant vapor to reach, they provide an accurate method of monitoring the sterilization status of the articles inside the container 100.

The sensitivity of the biological indicator and chemical indicator can be adjusted by adding features well known to those having ordinary skill in the art. A variety of such features are known which slow down the diffusion of sterilant. One example would be the STERRAD® Biological Indicator (BI) Test Pack, available from Advanced Sterilization Products (Irvine, Calif.).

In the present embodiment, upon completion of the sterilization cycle the cartridge 120 may be removed from the cartridge holder 126 to determine chemical and biological efficacy of the sterilization process. As opposed to prior art, however, the biological and/or chemical indicators can be removed from the container 100 without disturbing the sterilized state of the articles inside the sterilization container 100. Since the gas permeable layer 128 only allows the passage of the sterilant vapor, removal of the cartridge 120 from the holder 126 will not break the microorganism-impermeable seal of the container 100.

Referring now to FIG. 1C, there is shown a modified form of the embodiment shown in FIG. 1A. In this embodiment, the biological indicator 122 and/or chemical indicator 124 are placed into a housing 126 with an openable or removable door 121. This modified form of this first embodiment can otherwise be constructed and used in accordance with the description provided above.

In addition, it is particularly advantageous to use the biological and chemical indicators 122 and 124 in separate cartridges. In such case, the chemical indicator may be furnished with a translucent or clear window which can display a written message, such as "PROCESSED" or a symbol when the sterilization cycle is completed. Therefore, when the biological indicator is removed for detection, the chemical indicator may remain on the container and display the message to avoid any confusion during the storage. Alternatively, if the sterilization process uses more than one sterilant source, the number of chemical indicators can be increased accordingly. For example, if two chemicals are used as sterilant sources, the cartridge holder can be configured to have two chemical cartridges indicators and one or more biological indicator cartridges.

Figure 2:
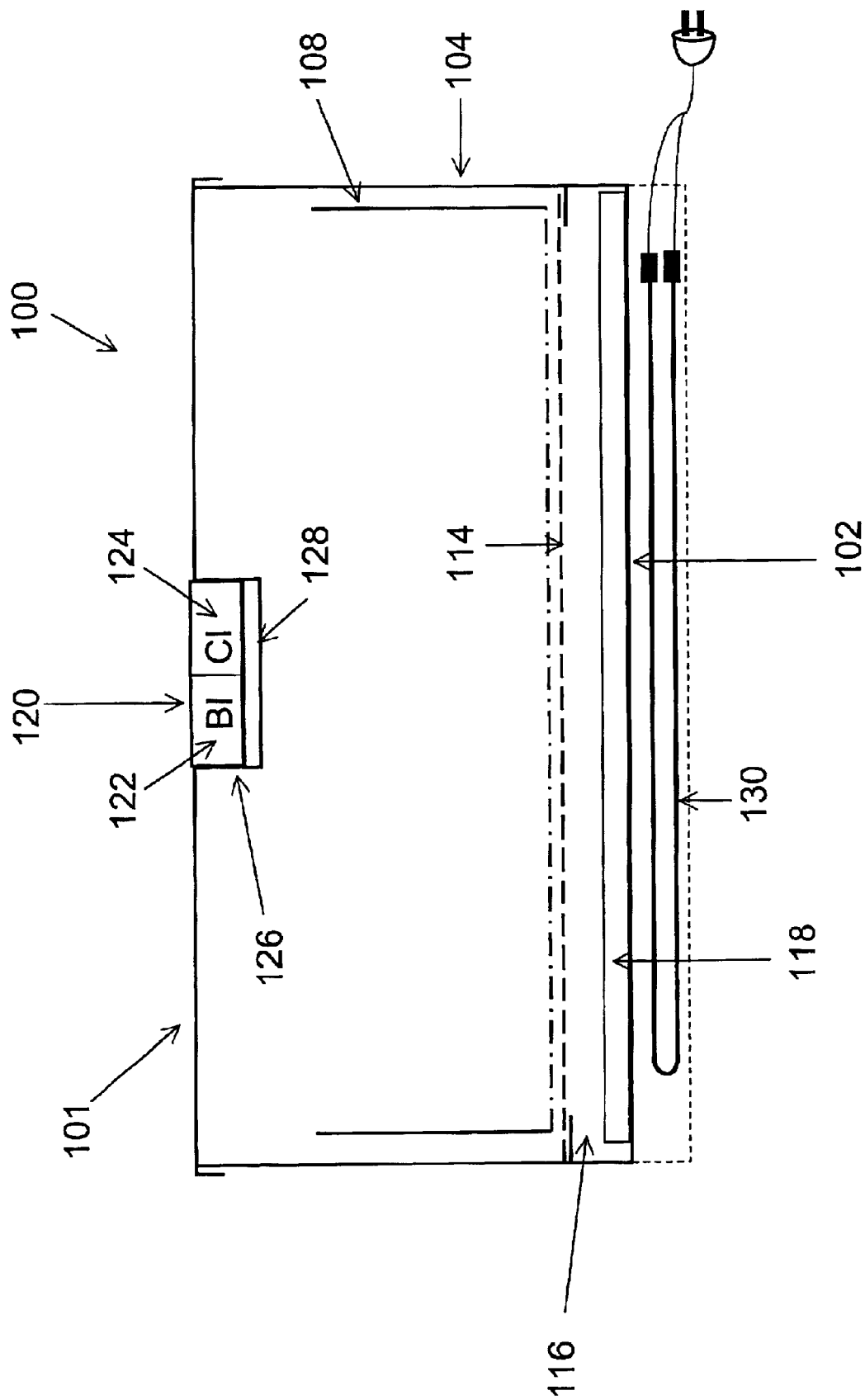
FIG. 2 is a schematic view of a second embodiment of the system wherein the sterilization container comprises a heating source.

As will be explained more fully in the following embodiments, the release of the sterilant gas can be enhanced using heat or vacuum. FIGS. 2–9C illustrate alternative embodiments of the present invention. FIG. 2 illustrates a second embodiment of the sterilization system comprising the sterilization container 100 and a heat source 130. In accordance with the principles of the present invention, the heat source 130 may be configured as a part of the container 100 or positioned adjacent to the container 100 without being a part of the container 100. In this embodiment, the heat source 130 may be a heat element comprising a resistant wire which is attached to the bottom portion 102 of the sterilization container 100. Heat from the heat element 130 enhances the vaporization of the sterilant source 118 in the sterilant housing 116 and thereby enhancing the sterilization of the articles in the container 100.

Figure 3:
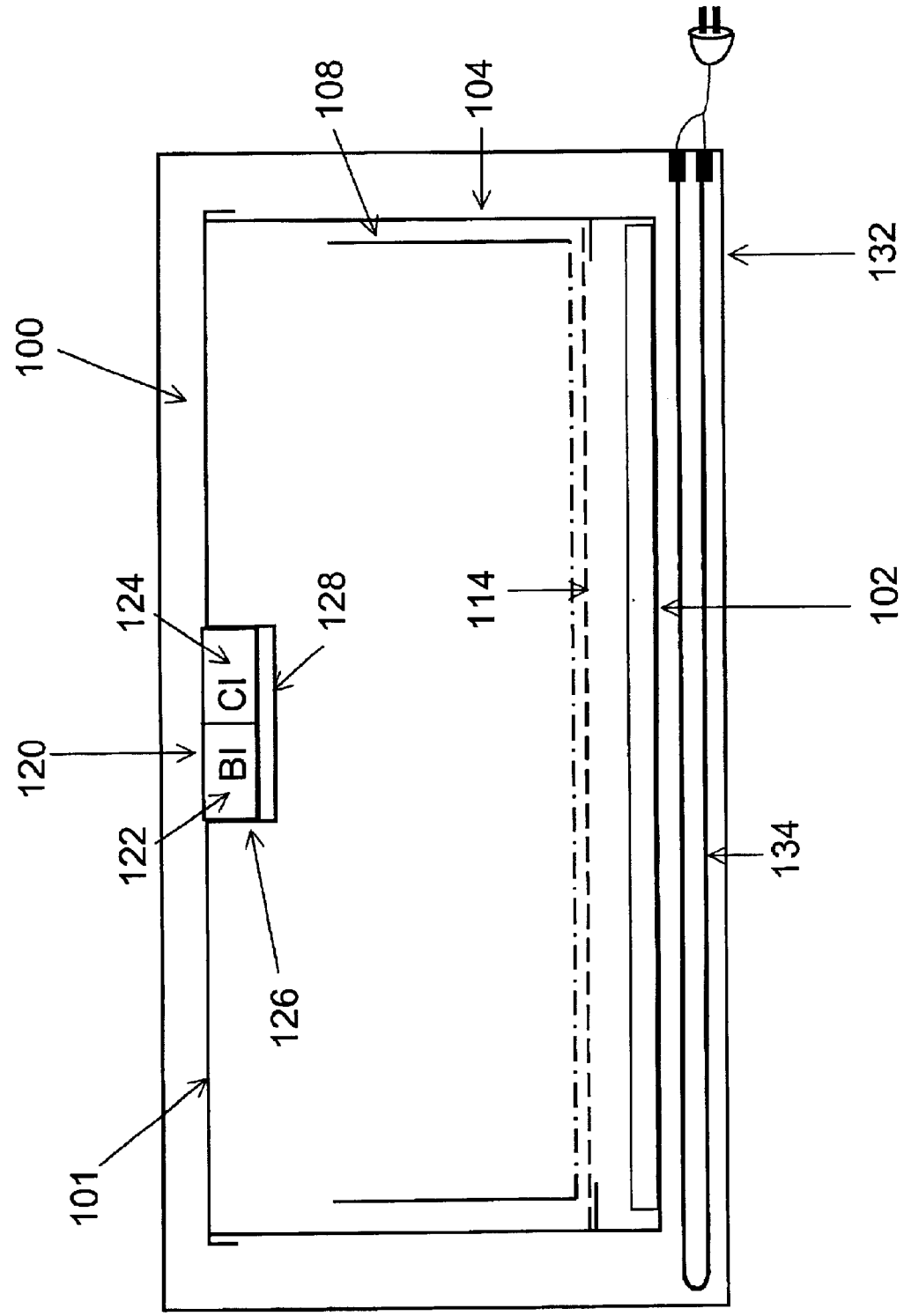
FIG. 3 is a schematic view of a third embodiment of the system wherein the sterilization container is placed into an oven.

FIG. 3 illustrates a third embodiment of the sterilization system comprising the sterilization container 100 placed into a third container 132. The third container 132 may be an oven having a heat source 134. In accordance with the principles of the present invention, the heat source 134 of the oven 132 may comprise infrared (IR) heating, radio frequency (RF) heating, microwave heating or resistant heating by heating elements. In the preferred embodiment, heating is provided by the heating elements 134.

Figure 4:
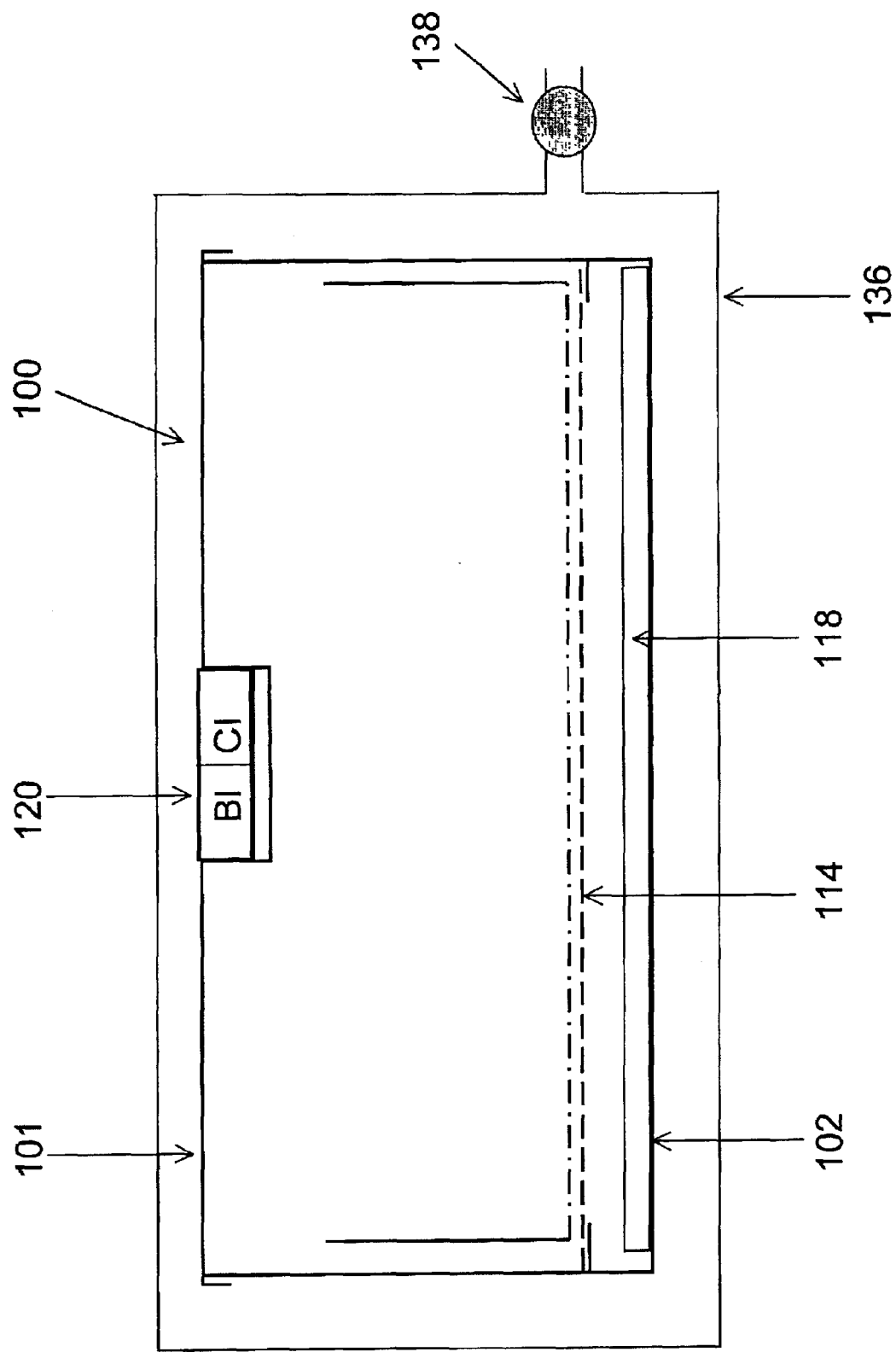
FIG. 4 is a schematic view of a fourth embodiment of the system wherein the sterilization container is placed into a vacuum chamber.

FIG. 4 illustrates a fourth embodiment of the sterilization system comprising the sterilization container 100 placed into a vacuum chamber 136 which is connected to a vacuum source (not shown) through a vacuum valve 138. The vacuum may also be used to enhance the vaporization of the sterilant source 118. Once the sterilization process is completed, the vacuum may also be used to remove the sterilant residues left on the articles.

Figure 5:
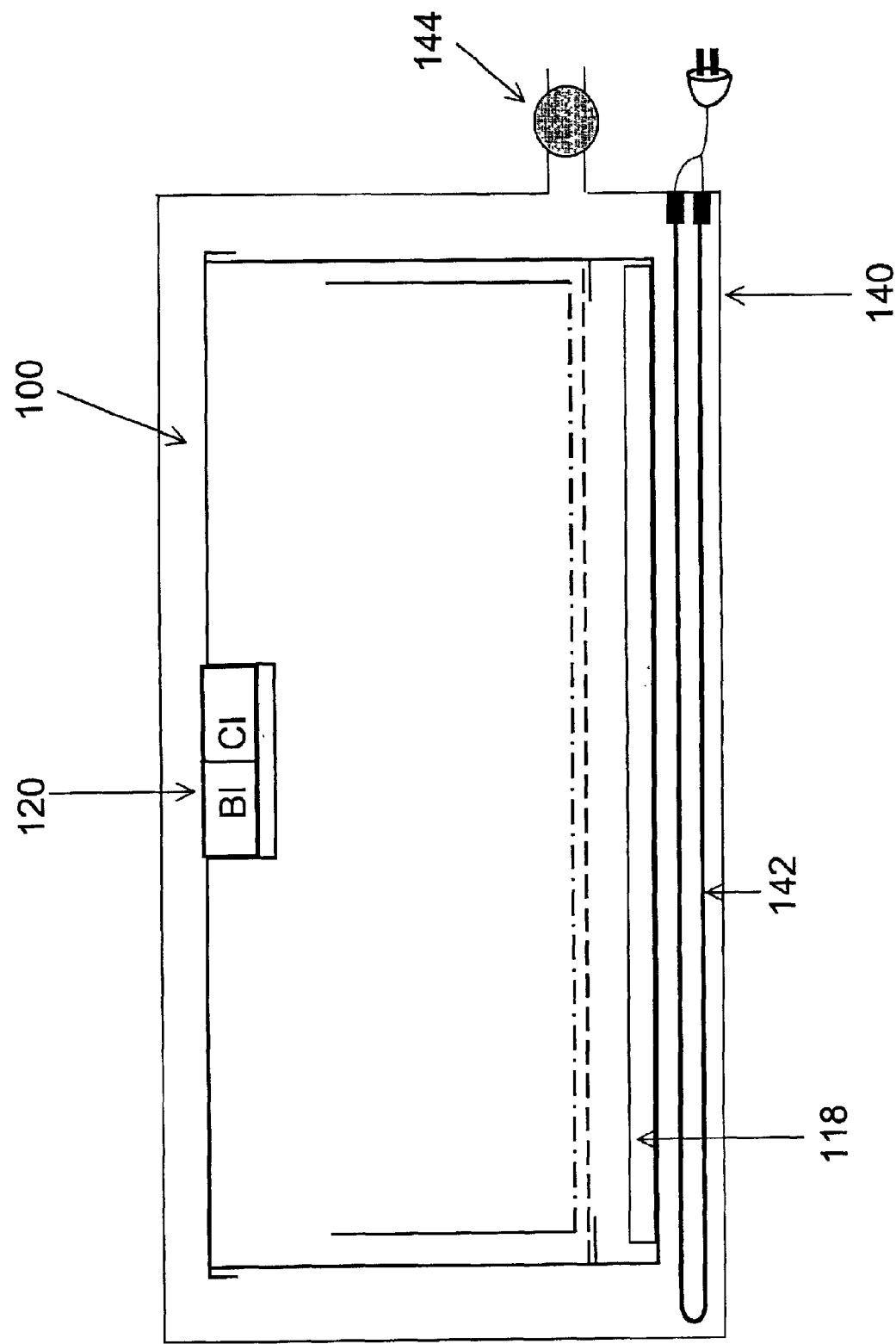
FIG. 5 is a schematic view of a fifth embodiment of the system wherein the sterilization container is placed into a vacuum oven.

FIG. 5 illustrates a fifth embodiment of the sterilization system comprising the sterilization container 100 placed into a vacuum oven 140. The vacuum oven is connected to a vacuum source (not shown) through a vacuum valve 144. The vacuum oven also comprises a heat source 142. In this embodiment, the combined effect of the vacuum and the heat enhances the vaporization of the sterilant source 118.

Figure 6A:
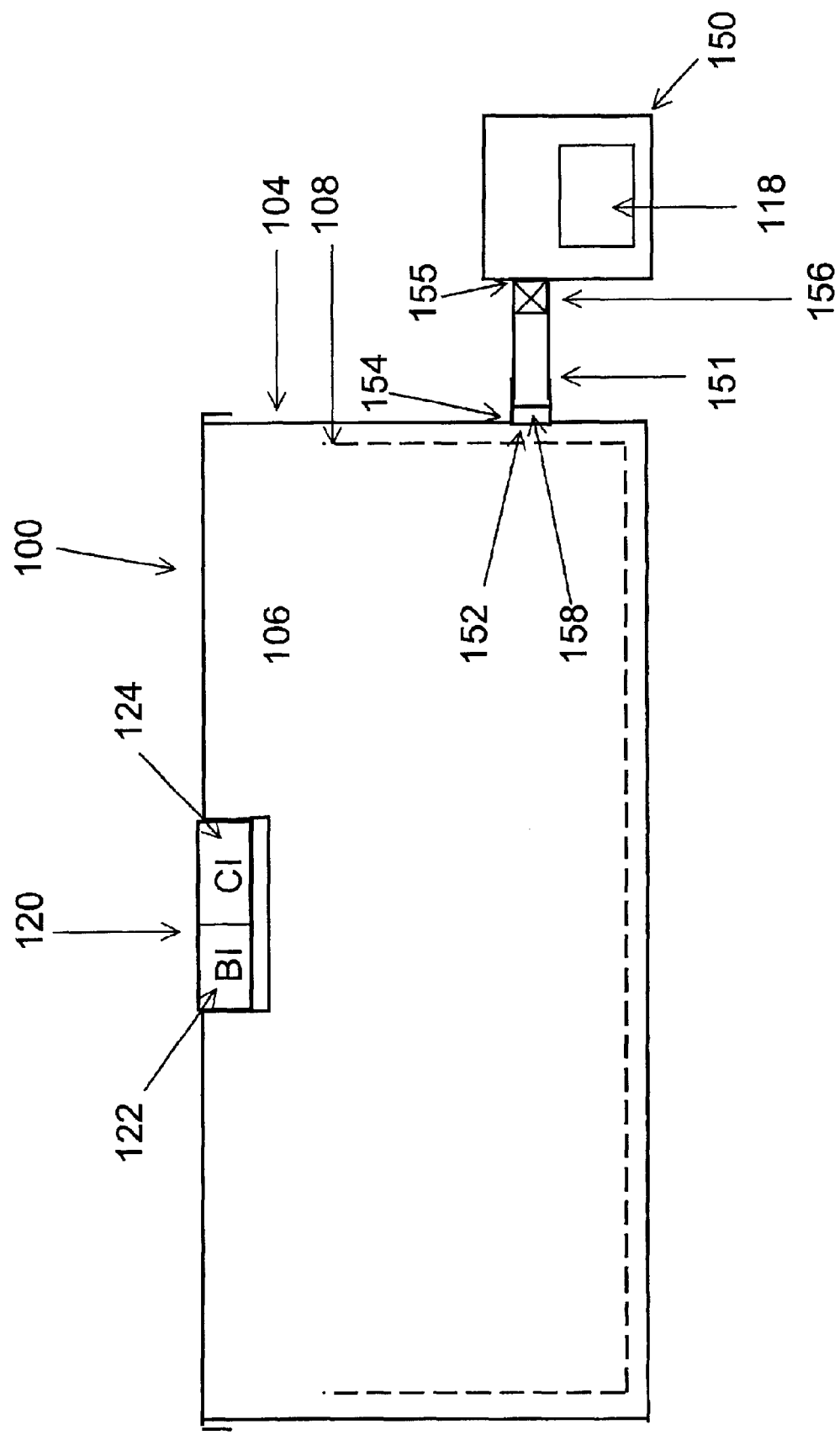
FIG. 6A is a schematic view of a sixth embodiment of the system wherein the sterilization container comprises a separate sterilant enclosure.

FIG. 6A illustrates a sixth embodiment of the sterilization system comprising the sterilization container 100. In this embodiment, the sterilization container 100 is modified to include an attachable sterilant enclosure 150 with the sterilant 118. Therefore, in this embodiment, the rack 114 and the sterilant housing 116 (See FIGS. 1A–5) shown in the previous embodiments are excluded. Accordingly, the sterilization container 100 is connected to the sterilant enclosure 150 by a connector 151. In this embodiment, a first end 154 of the connector 151 is connected to an opening 152 on the peripheral wall 104, while a second end 155 of the connector 151 is connected to the sterilant enclosure 150 through an optional valve 156 on the enclosure 150. A gas permeable membrane 158 further covers the opening 152 so that when the sterilant enclosure 150 is detached from the container 100, the sterility of the load in the container housing 106 is maintained. In the process of the present embodiment, the sterilant vapor from the sterilant source 118 passes through the valve 156 and gas permeable membrane 158 and enters the container 100 for sterilizing articles. For better diffusion, the inner tray 108 can have perforated walls. Similar to the previous embodiments, the biological and chemical indicators 122 and 124 can be attached to or detached from the container 100 without disturbing the sterility of the articles in the container 100.

Figure 6B:
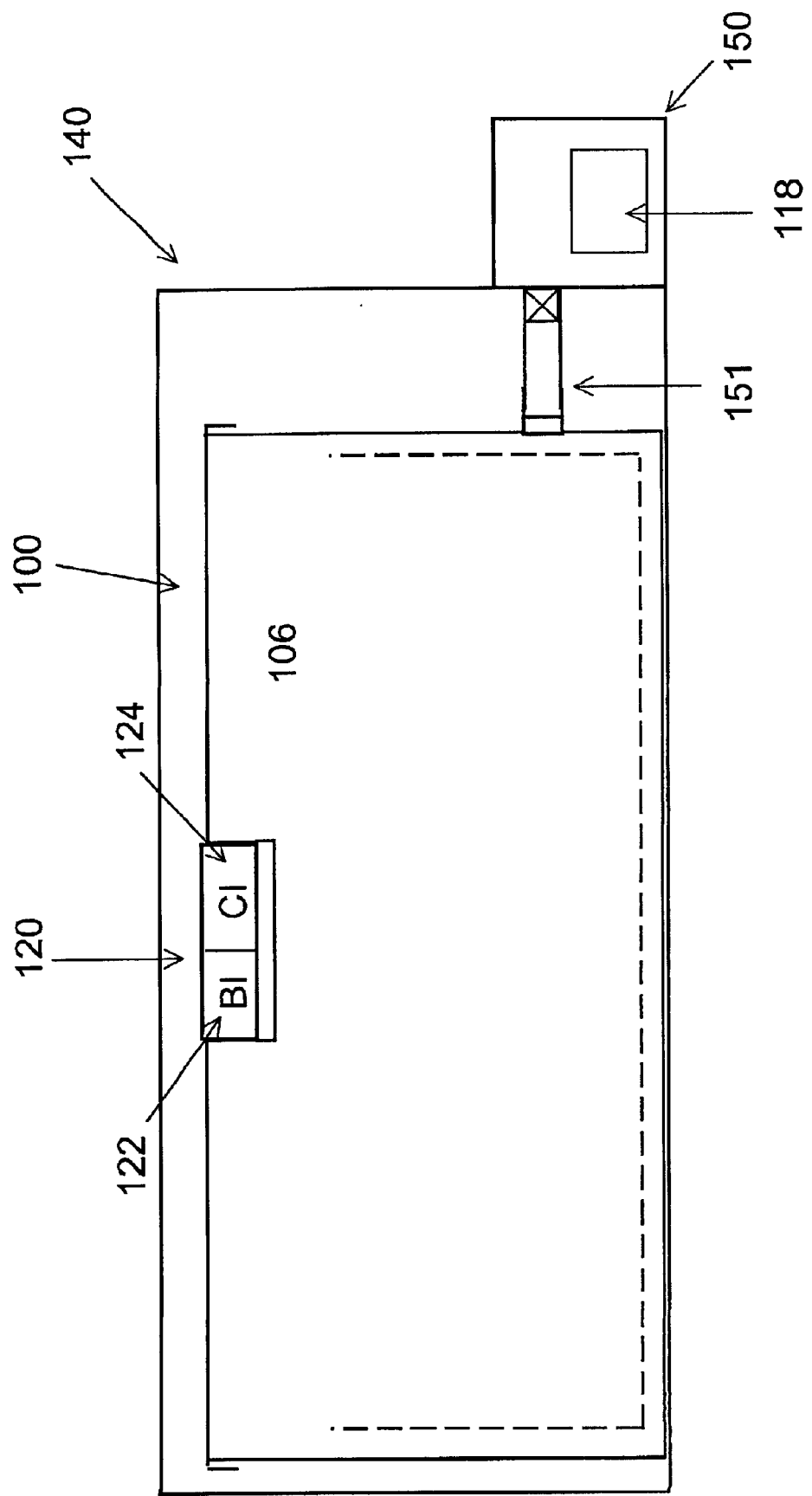
FIG. 6B is a schematic view of the system shown in FIG. 6A wherein the sterilization container with the separate sterilant enclosure is placed into a vacuum oven.

Within the scope of this invention, it will be appreciated that the present embodiment may also comprise all the features and options of the previous embodiments. For example, as in the second embodiment, the sterilant enclosure 150, as attached to the container 100, may be heated by a heat source to enhance the vaporization of the sterilant source 118 (See FIG. 2). Similar to the third, the fourth and the fifth embodiments, the container can be placed into a third container which may be an oven 132, vacuum chamber 136 or a vacuum oven 140 (See FIGS. 3–5). In all above embodiments, after the sterilization the sterilant enclosure 150 may be detached from the container 100 for storage purposes. Similarly, by suitable modifications in the oven 132, the vacuum chamber 136 and the vacuum oven 140, the sterilant enclosure may be integrated with the containers 132, 136 and 140. As illustrated in FIG. 6B, for example, when the container 100 is placed into the third container, such as a vacuum oven 140, the sterilant enclosure 150 is connected to the container 100 through conductor 151 as in the manner shown in FIG. 6B. The enclosure 150 can be heated to a different temperature than the vacuum oven 140.

Figure 7:
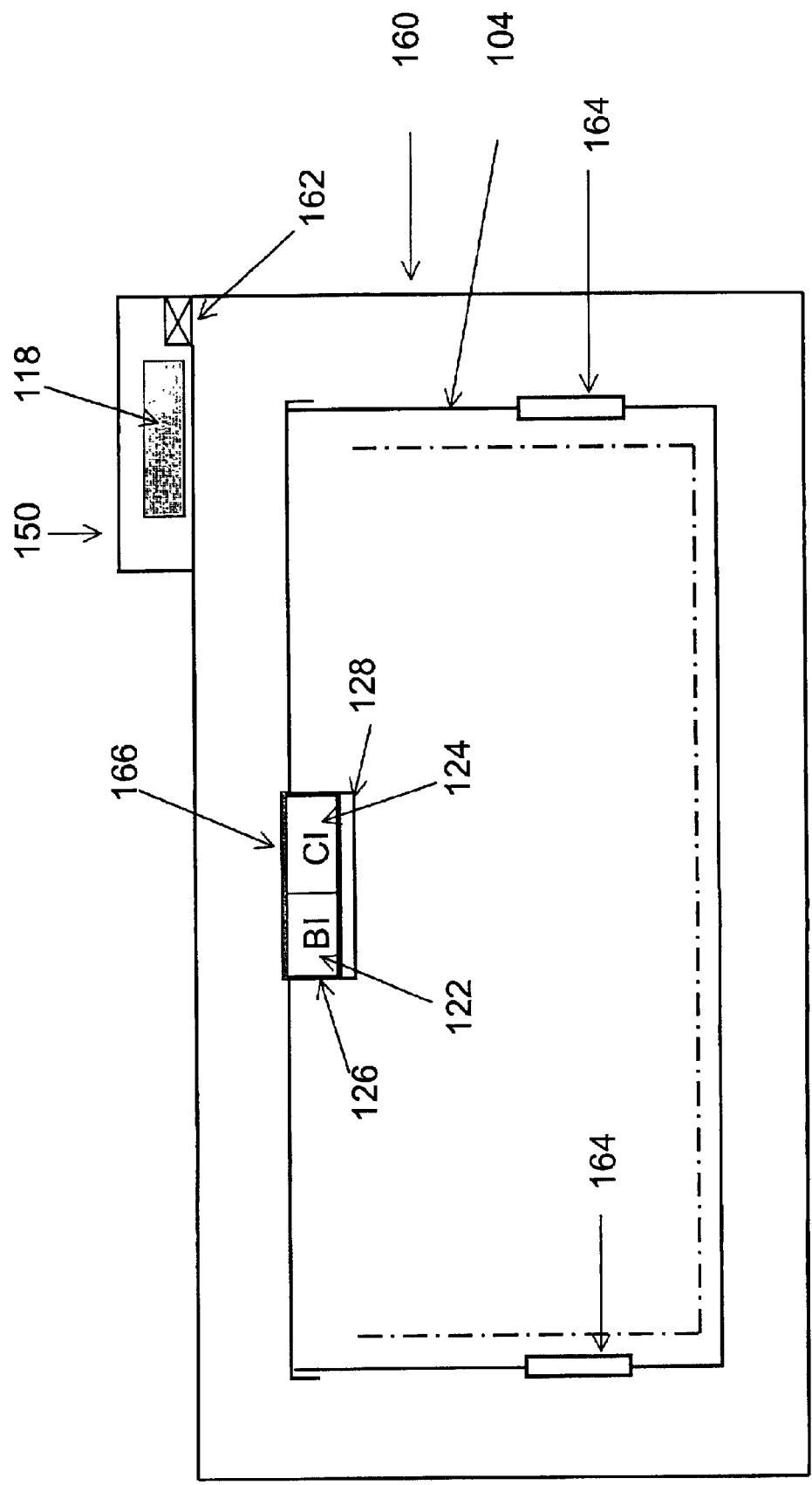
FIG. 7 is a schematic view of a seventh embodiment of the system wherein the sterilization container is placed into another container having an attached sterilant enclosure.

FIG. 7 shows a seventh embodiment of the sterilization system comprising the sterilization container 100 placed into a third container 160 and the enclosure 150 is attached to the container 160, such as by being an integrated part thereof. However, as opposed to previous embodiment, in this embodiment there is no direct connection between the sterilant enclosure 150 and the sterilant container 100. A number of gas permeable membrane covered inlets 164 are positioned on the peripheral wall 104 of the container 100. Further, top of the cartridge holder 126 may be sealed with a removable gas impermeable material 166 so as to expose indicators 122 and 124 only to the sterilant vapor diffusing through the gas permeable membrane 128. An exemplary gas impermeable material can be Mylar, metal foil, glass or adhesive tape. In the process of this embodiment, the sterilant gas first diffuses into the container 160 through inlet 162 and fills the container 160. The inlet 162 can be configured as a valve. As the process progresses, the sterilant gas diffuses from the enclosure 150 through the inlet 162 and into the container 160. From the container 160, the gas diffuses through the permeable membrane 164 into the container 100, through the permeable membrane 128 and into the cartridge 120, so as to contact the indicators 122 and 124. At the end of the process cycle, the gas impermeable material can be removed and the cartridge can be taken out for inspecting indicators 122 and 124.

As illustrated in FIG. 8, in an eighth embodiment, the sterilization system comprises the sterilization container 100 and the sterilant enclosure 150 as described in the sixth embodiment. In an effort to enhance the accuracy of the information provided from the indicators 122 and 124, in this embodiment, the cartridge holder 126 is positioned at a remotest location from the sterilant enclosure 150 containing sterilant source 118. Referring to FIG. 8, this location is on the peripheral wall 104 and at the opposite side of the container 100. A fan 160 can optionally be provided to circulate sterilant throughout the container 100. As previously explained, since the indicators 122 and 124 are the last place for sterilant vapor to reach, they provide an accurate method of monitoring the sterilization status of the articles inside the container 100.

As illustrated in FIG. 9A, in a first alternative embodiment, the sterilization system comprises an alternative container 200. In this embodiment, the alternative container 200 is preferably a flexible enclosed container, such as a pouch, which is comprised of a gas impermeable sheet material 202 defining a housing 204 to have articles to be sterilized (not shown). An exemplary gas impermeable sheet material may be preferably Mylar™ (polyester), metal foil, polymer film materials such as polypropylene or polyethylene films. The gas impermeable sheet can also be multilayer of film with or without lamination or coating. The flexible container 200 of this invention further comprise a first window 206, second window 208 and an opening 210. The first and second windows 206 and 208 are comprised of gas permeable materials, and preferably positioned at the opposite ends of the pouch 200. Articles to be sterilized are placed into the container 200 through the opening 210. This opening 210 may be a resealable opening for multiple use of the container 200 or may be a non-resealable opening for a single use.

A sterilant source cartridge 212 may be sealably placed onto the first gas permeable window 206 and secured using various fastening mechanisms such as double-sided tape, snap-on connectors or the like. As shown in FIG. 9B, the sterilant source cartridge 212 comprises a gas permeable bottom 216, a gas impermeable top 214 and peripheral side walls 213 defining a sterilant housing 215. For shipping and safe handling purposes, another gas impermeable layer 217 may be removably placed on the layer 216. However, before placing the cartridge onto the window 206, this impermeable layer 217 should be removed. In this embodiment, the gas permeable bottom 216 of the cartridge 212 is preferably sized and shaped to fit over the window 206. Referring to FIG. 9A, when the cartridge 212 is placed onto the gas permeable window 206, the bottom gas permeable layer 216 faces towards the window 206 on the flexible container 200. Therefore, when a sterilant source in the cartridge 212 releases a sterilant vapor, the vapor diffuses via the bottom layer 216 and the window 206 into the container 200 having articles to be sterilized.

As illustrated in FIG. 9C, a process monitoring cartridge 218 comprising the biological and chemical indicators 122 and 124 may be sealably placed onto the second gas permeable window 208, as in the manner described for the sterilant cartridge 212. As shown in FIG. 9C, the process monitoring cartridge 218 is comprised of a gas permeable bottom 220, a gas permeable removable top 221 and a body 222 comprising the biological and/or chemical indicators 122 and 124. In operation, the sterilant gas released from the sterilant cartridge 212 diffuses into the container housing 204 (in the direction of the arrows) and reaches at the monitoring cartridge 218 through the gas permeable window 208. Similar to previous embodiments, the flexible container 200 of the present invention can be also used in the oven 132, the vacuum chamber 136 or a vacuum oven 140.

Figure 9D:
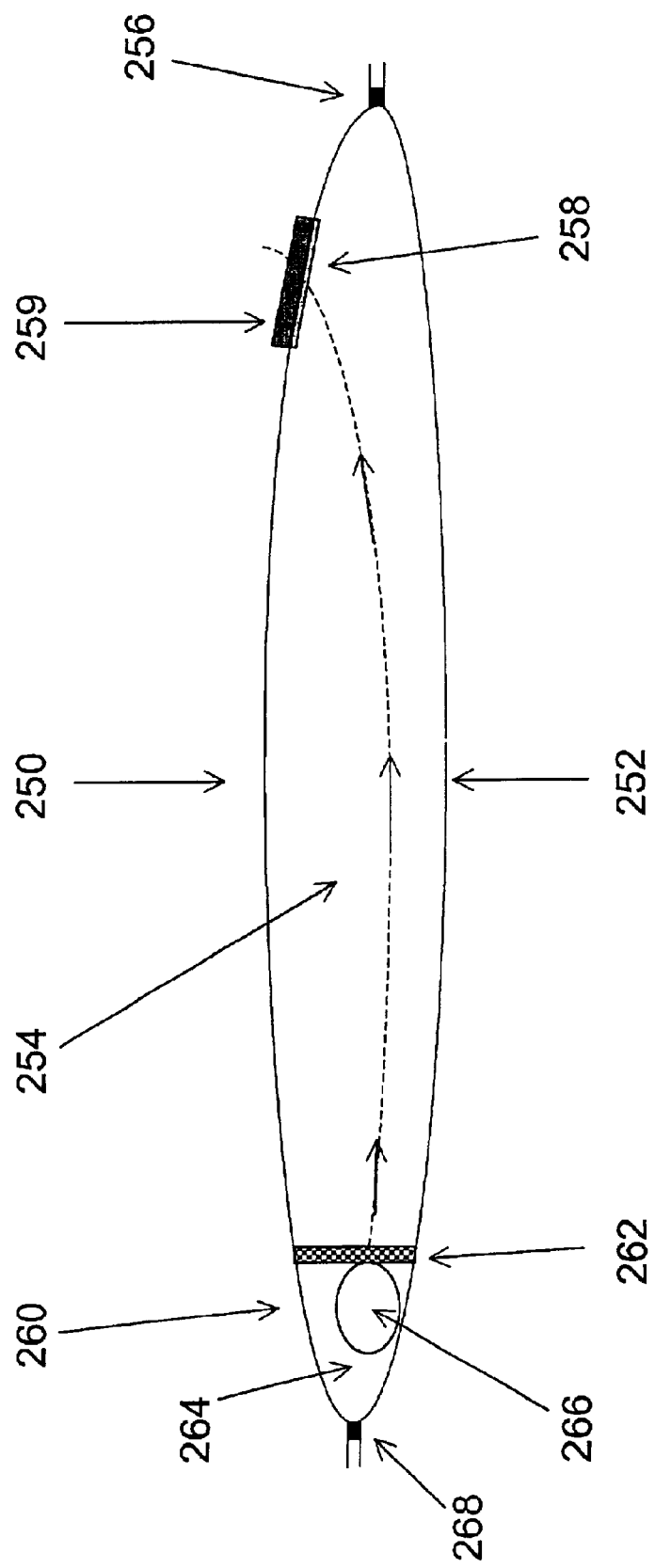
FIG. 9D is a schematic view of another alternative embodiment of the system with one window and sterilant inside a pouch behind a gas permeable membrane.

As illustrated in FIG. 9D, in a second alternative embodiment, the sterilization system comprises a flexible enclosed container 250. Similar to the pouch 200 of the previous embodiment, the flexible container 250 also comprises a gas impermeable sheet material 252 (such as those materials given above) defining a container housing 254 and an opening 256 to place articles (not shown) into the container 250. However, in this embodiment, the container 250 comprises only one gas permeable window 258 on which a process monitoring cartridge 259 is placed, and a sterilant enclosure 260 attached to a gas permeable wall portion 262 of the flexible container 250. In this embodiment, the sterilant enclosure 260 is preferably a flexible sterilant enclosure comprising a sterilant housing 264 which is separated from the container housing 254 by the gas permeable wall portion 262. A sterilant source 266 may be placed into the housing 264 through an optional opening 268. This optional opening 268 may be a resealable opening for multiple use of the container 250 or may be a non-resealable opening for a single use. Similar to the previous embodiment, in operation, the sterilant gas released from the sterilant source 266 diffuses through the gas permeable wall portion 262 into the container housing 254, and reaches at the monitoring cartridge 259 (following arrows in FIG. 9D) through the gas permeable window 258.

Figure 10:
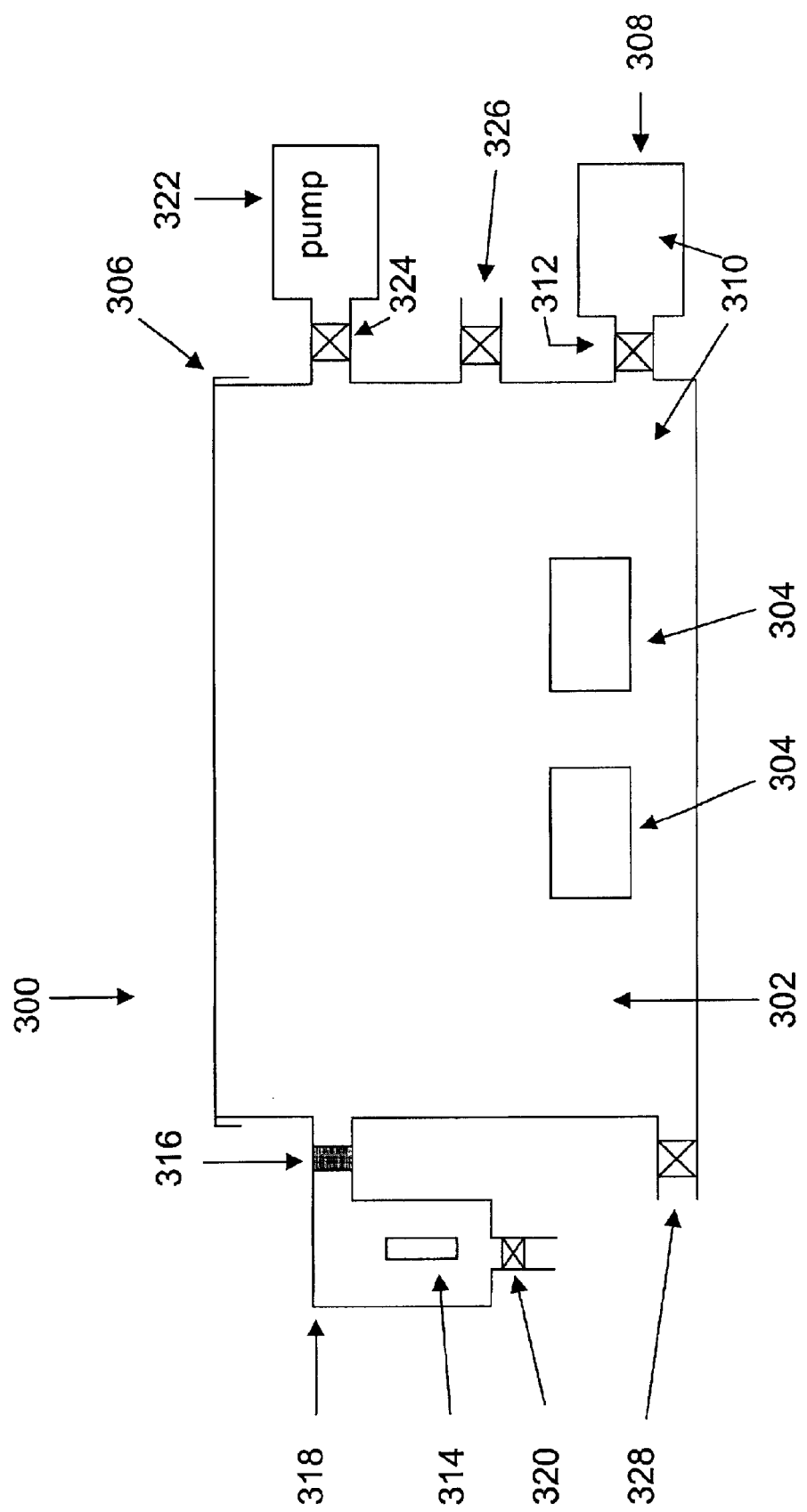
FIG. 10 is a schematic view of a further embodiment of the system.

FIG. 10 illustrates a further embodiment of the invention. A container 300, has an interior space 302, with an article 304 to be sterilized therein. The container 300 may be a rigid container formed of a material suitable for exposure to the sterilization environment, such as a liquid crystal polymer, or may be flexible such as a pouch. So as to protect the sterility or cleanliness of the article 304 or articles, it must be impermeable to microorganisms. The container 300 is shown with a lid 306, but any means of placing the articles 304 into the container 300 and closing them inside as is known in the container art either presently, or during the life of this patent may be employed.

A source 308 of an antimicrobial agent 310 is provided. FIG. 10 shows the source 308 as a separate enclosure attached to the container 300 but most typically the container 300 will be placed into a sterilization chamber (not shown) which is filled with the antimicrobial agent 310, such as a steam sterilizer, or hydrogen peroxide/plasma sterilization chamber as is known in the art. The source 308 is separated from the interior space 302 by a valve 312, thereby allowing ingress of the antimicrobial agent while preventing ingress of microorganisms when the sterilization is completed. Alternatively and preferably, a semi-permeable barrier may be employed.

An indicator 314 is in fluid communication with the interior space 302 past a semipermeable barrier 316 of a vapor permeable, microorganism impermeable material. The indicator 314 is contained within a housing 318 having a valve 320. The entire housing 318 may be detachable from the container 300 or the indicator 314 may be removable from the housing 318. Alternatively, the indicator 314 may connect directly to the container 300 through the barrier 316, thus dispensing with the housing. Of course, a valve could substitute for the barrier 316. Preferably, the indicator 314 is exposed to the antimicrobial agent only through the interior space 302.

The container 300 may comprise the sterilization chamber for purposes of sterilizing the articles 304. FIG. 10 shows the container 300 having a pump 322 connected thereto through an isolation valve 324. The pump 322 draws a vacuum on the interior space 302 which can vaporize a liquid sterilant in fluid communication with the interior space 302 by virtue of being disposed therein or being connected thereto as shown with the source 308. The container 300 may also be used for washing the articles 304 and be provided with a valved fluid inlet 326. A drain valve 328 is also shown. Valves 328 and 320 allow liquid to drain from the container 300 and housing 318. Therefore, suitable fluids for use in this invention include, but are not limited to: liquid, mist, aerosol, gas or vapor. Additionally, the fluid can also include the gas plasma.

Figure 11:
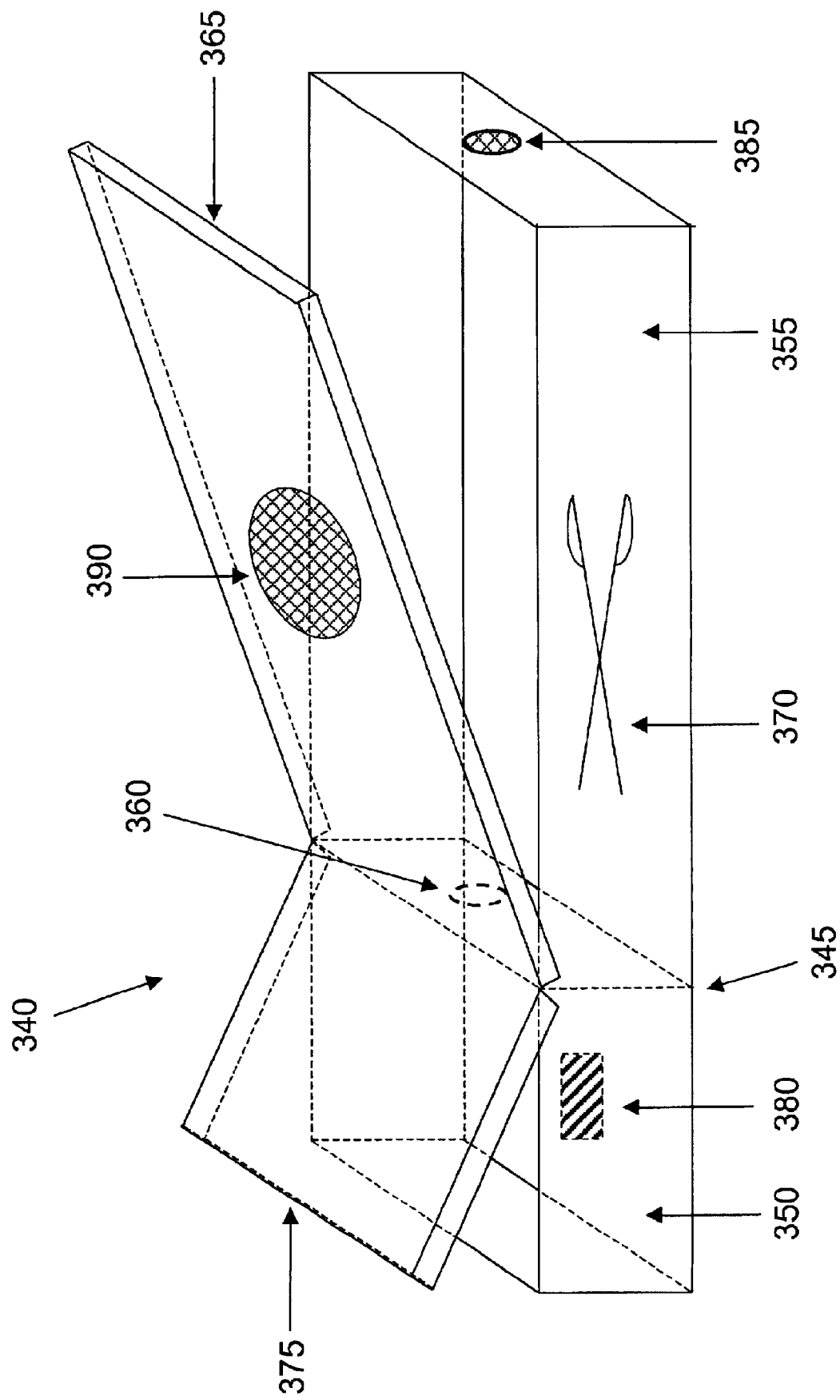
FIG. 11 is a schematic view of an enclosure having hinged lid with two areas separated with a partition.

FIG. 11 shows a container 340 having a partition 345 to separate the container into two areas 350 and 355. Areas 350 and 355 are in fluid communication through an opening 360 on the partition 345. Optionally, the opening 360 has a gas or vapor permeable and microorganism impermeable barrier. Area 355 having a lid 365 contains an article 370 to be sterilized or disinfected, and area 350 having a lid 375 contains at least one indicator 380. The indicator 380 can be a chemical indicator and/or a biological indicator. Suitable biological indicators include a packaged substrate containing microorganisms or a self-contained biological indicator having growth medium to support the growth of the microorganisms, or perhaps enzymes indicative of microorganisms. Both lids 365 and 375 can be attached near the top of the partition 345. The mechanism to attach the lids 365 and 375 can be achieved with many conventional means such as heat-seal or by hinging the lid to the container. The lids can also be attached on other side of the container. Preferably, at least a portion of the container, perhaps including the lids is clear or translucent, such that the user can view the article and/or the indicator in the container. The container 340 further comprises at least one gas or vapor permeable and microorganism impermeable window 385 or 390 into area 355. The container 340 does not have any window on the walls around the area 350 except the window on the partition 360. The window 385 or 390 allows the antimicrobial agent to diffuse from outside of the container 340 into the area 355 containing the article 370. The antimicrobial agent then diffuses from the area 355 containing the article 370 to the area 350 containing the indicator 380. The antimicrobial agent has to diffuse from outside of the container 340 indirectly into the area 350 containing the indicator 380 through the area 355 containing the article 370. Therefore, the antimicrobial agent diffuses into the container 340 through area 355 and contacts the article 370 before it diffuses into area 350 and contacts the indicator 380. With the gas or vapor permeable and microorganisms impermeable barrier on the opening 360, the indicator can be removed after the sterilization or disinfection process by opening the lid 375 without the risk of contaminating the article 370 in the area 355. If the partition does not have the gas or vapor permeable and microorganisms impermeable barrier on the opening 360, then the indicator 380 needs to be stored in the container 340 with the article 370 until the user is ready to use the article 370 in the container 340.

Figure 12:
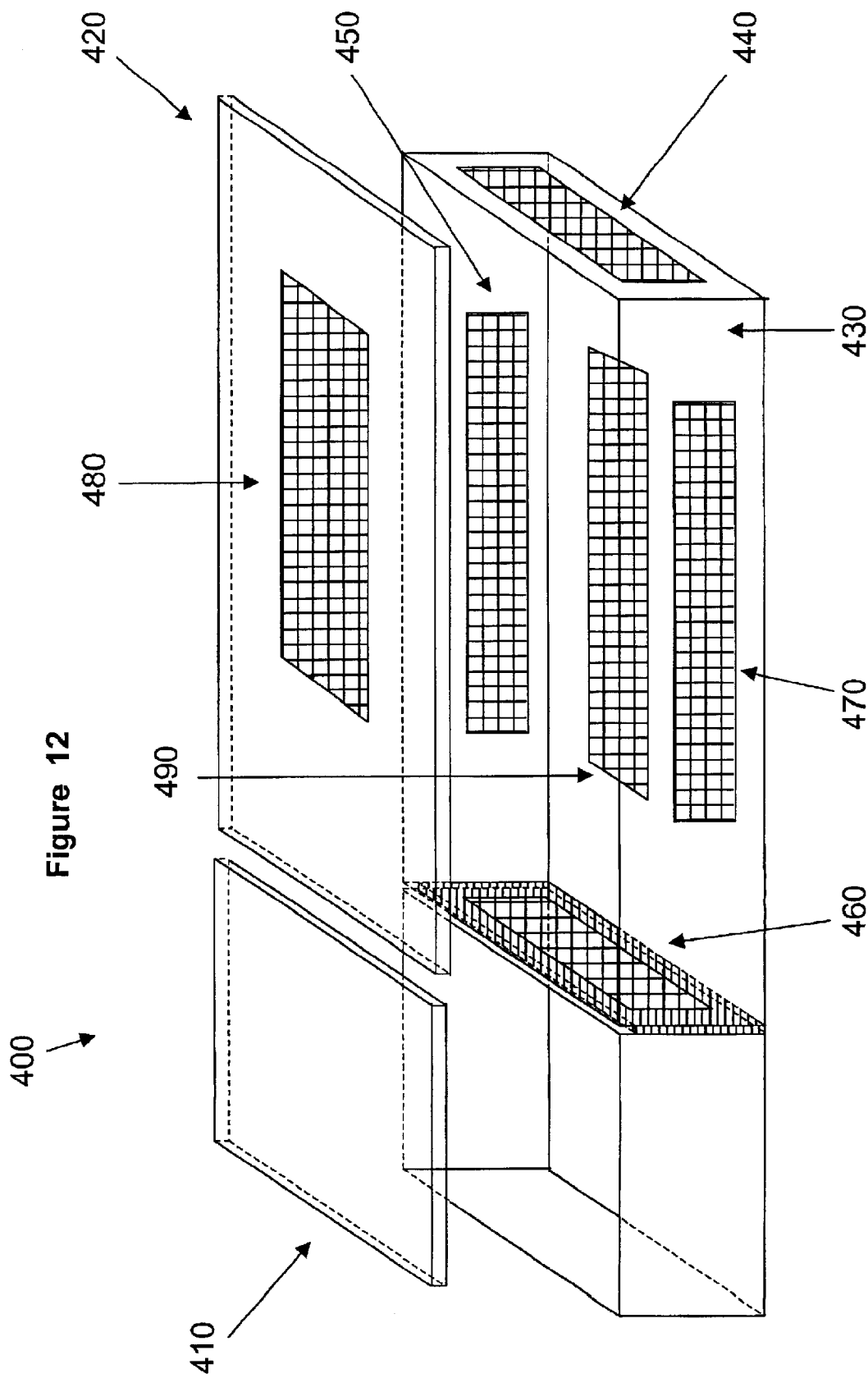
FIG. 12 is a schematic view of an enclosure having removable lid with two areas separated by a partition.

FIG. 12 shows a container 400 similar to the container 340 of FIG. 11 but with two removable lids 410 and 420. The area 430 has gas or vapor permeable and microorganism impermeable windows 440, 450, 460, 470, 480, 490 on all six sides of walls. Actually, one gas or vapor permeable and microorganism impermeable window is sufficient to diffuse the antimicrobial agent into the area 430. Six windows can shorten the time required to diffuse the required antimicrobial agent into the container 400.

Figure 13:
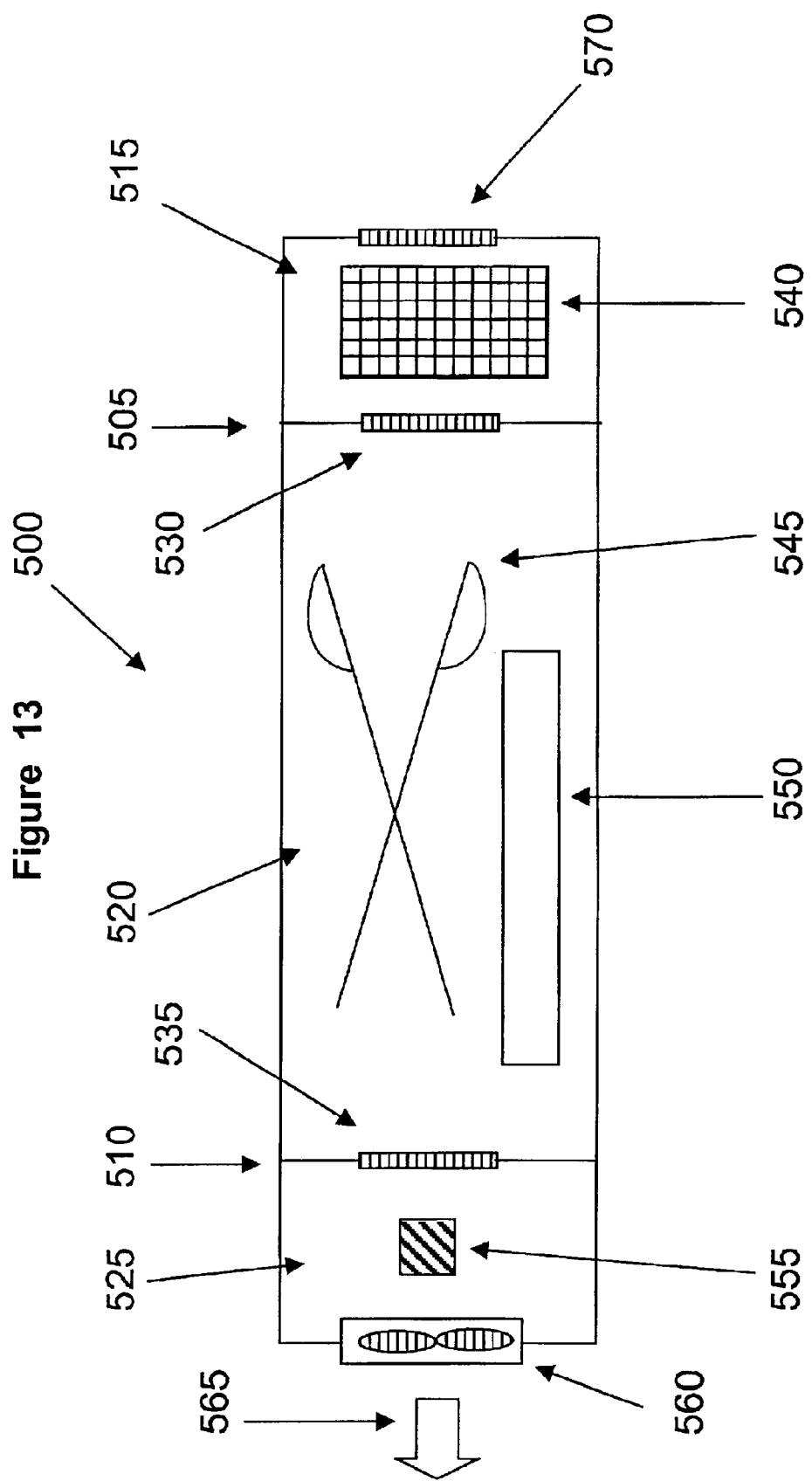
FIG. 13 is a schematic view of an enclosure having a directional flow of antimicrobial agent through the article to be processed and the indicator.

FIG. 13 shows a container 500 with two partitions 505 and 510 which divide the container 500 into three compartments 515, 520, and 525. The compartment 515 is in fluid communication with the compartment 520 through the port 530 on the partition 505, and the compartment 525 is in fluid communication with the compartment 520 through the port 535 on the partition 510. Preferably, either or both ports 530 and 535 have a gas or vapor permeable and microorganism impermeable barrier. Compartment 515 contains the antimicrobial source 540 which provides the antimicrobial agent, compartment 520 has the devices 545 and 550 to be disinfected or sterilized, and compartment 525 contains at least one indicator 555. The compartments 515, 520, and 525 can share a common lid or have its own lid. The antimicrobial agent can be a gas or vapor generated from a source of liquid or solid. The antimicrobial agent can be steam, ethylene oxide, chlorine dioxide, hydrogen peroxide, peracetic acid, performic acid, formaldehyde, glutaraldehyde, ozone or other suitable vapor. Preferably, the antimicrobial agent comprises hydrogen peroxide, and the antimicrobial source 540 is a liquid comprising hydrogen peroxide or a solid which releases hydrogen peroxide vapor. Preferably, the antimicrobial source 540 is packaged in a gas or vapor permeable and liquid impermeable barrier which retains the antimicrobial source 540 and allows the diffusion of the antimicrobial agent. The device 550 can be a lumened device. The container further comprises a fan 560 and a window 570 to enhance the flow of the antimicrobial agent from compartment 515 through compartment 520 to compartment 525. The fan 560 can be operated by AC, DC or any other means. Preferably, the fan 560 is a battery-operated and self-contained fan with a switch to control the operation of the fan. The arrow 565 indicates the direction which the fan blows. The fan 560 can be located at other wall or in any of the compartments, as long as it can enhance the flow of the antimicrobial agent from the source 540 through the devices 545 and 550 to the indicator 555. More than one fan can be used to facilitate the flow of the antimicrobial agent. Additional fan(s) can also be used in the compartment 520 to help the uniform distribution of the antimicrobial agent over the devices 545 and 550 in the compartment 520. The container 500 can be placed into a heated and/or reduced-pressure environment to facilitate the release of the antimicrobial agent from the antimicrobial source 540.

Figure 14:
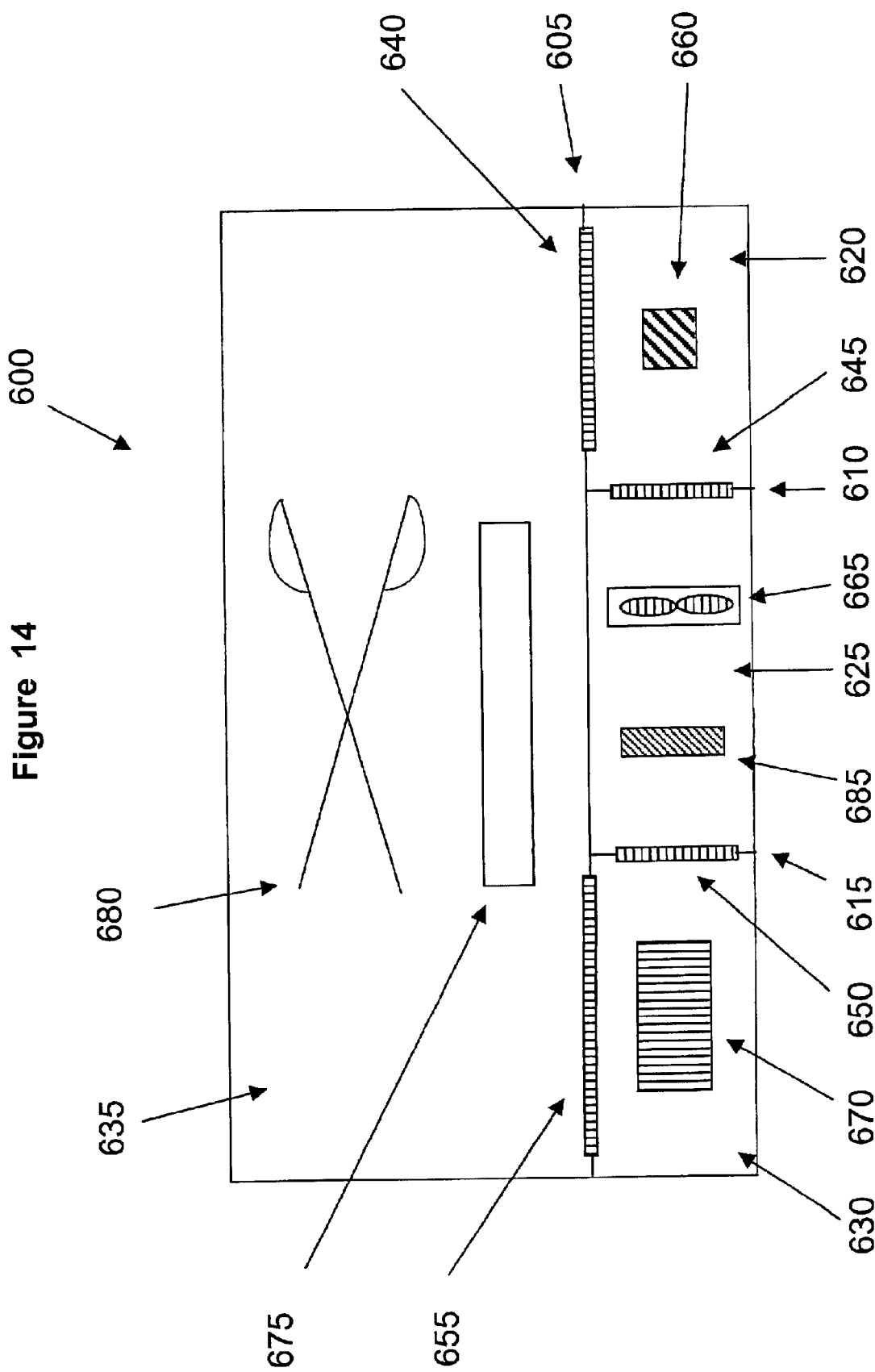
FIG. 14 is a schematic view of an enclosure having a fan to circulate the antimicrobial agent within the enclosure.

FIG. 14 shows a container 600 with partitions 605, 610, and 615 which separate the container into compartments 620, 625, 630, and 635. Compartments 620, 625, 630, and 635 are in fluid communication through the ports 640, 645, 650, and 655. Preferably, the ports 640 645, 650, and 655 have gas or vapor permeable and microorganism impermeable barrier. Compartments 620, 625, 630, and 635 contain an indicator 660, fan 665, antimicrobial source 670, and devices 675 and 680 to be processed, respectively. The compartments 620, 625, 630, and 635 can share a common lid or each one can have its own lid. The fan 665 circulates the antimicrobial agent from the antimicrobial source 670 through the devices 675 and 680, and then to the indicator 660. Unlike the container 500 of FIG. 13, the antimicrobial agent in the container 600 can be re-circulated and re-used. The container further comprises a heater 685 to help the circulation of the heated air in the container 600. The heated air can enhance the efficacy and the release of the antimicrobial agent from the antimicrobial source 670. More than one fan can be used to facilitate the circulation of the antimicrobial agent in the container 600, and to help the uniform distribution of the antimicrobial agent over the devices 675 and 680 in the compartment 635.

Figure 15:
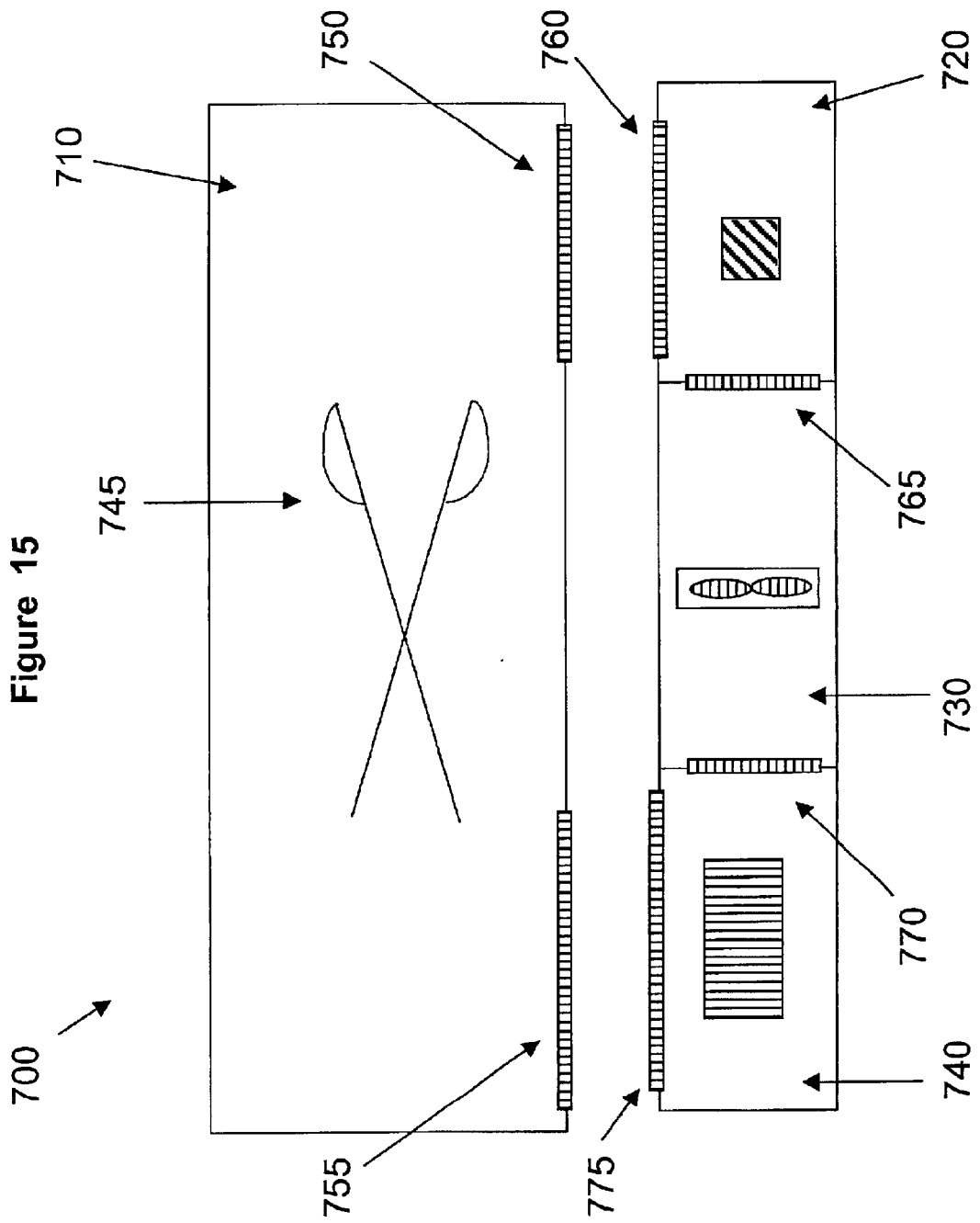
FIG. 15 is a schematic view of an enclosure having additional partition and interface for placing the lumen device.

FIG. 15 shows a container 700 which is similar to the container 600 of FIG. 14 except the compartments 710 can be attached and detached from the compartments 720, 730, and 740. The coupling of the compartment 710 to the other compartments 720, 730 and 740 does not need to be airtight. The parts can be snapped together, clipped together, attached with VELCRO hook and loop closure or tape, or any other conventional means. Optionally, the compartments 720, 730, and 740 can also be detached and attached to each other. Preferably, each attachable/detachable compartment has its own lid. In order to prevent the risk of contaminating the device 745 in the compartment 710 after the sterilization or disinfection process, the communication ports 750 and 755 need to be covered with gas or vapor permeable and microorganism impermeable barrier. The other ports 760, 765, 770, and 775 can be any openings with or without the gas or vapor permeable and microorganism impermeable barrier.

Figure 16:
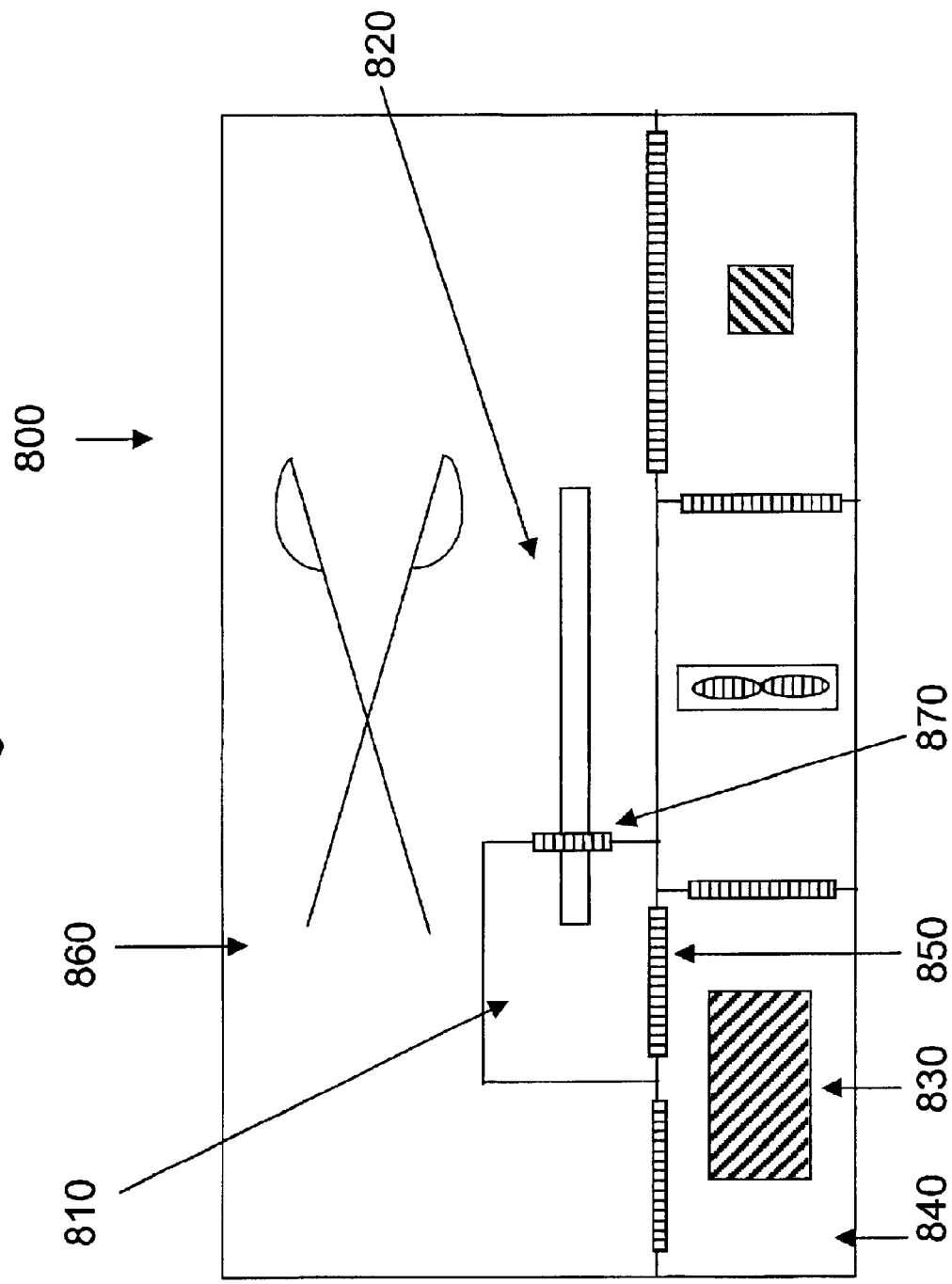
FIG. 16 is a schematic view of an enclosure having attachable/detachable compartment.

FIG. 16 shows a container 800 which is similar to the container 600 of FIG. 14 except there is an additional compartment 810 in the container 800 to contain one open end of the lumen device 820. This additional compartment 810 allows portion of the antimicrobial agent generated from the antimicrobial source 830 to diffuse from the compartment 840 through the port 850 into the compartment 810, and then through the lumen device 820 into the compartment 860. This additional compartment 810 helps the diffusion of the antimicrobial agent through the lumen device 820. The port 870 which holds the lumen device 820 can be a holder with an openable/closeable and/or controllable opening or any opening equipped with compressible, inflatable, or expandable material. A variety of holders or openings are described in the U.S. Pat. No. 6,083,458 which is incorporated herein by reference.

Figure 17:
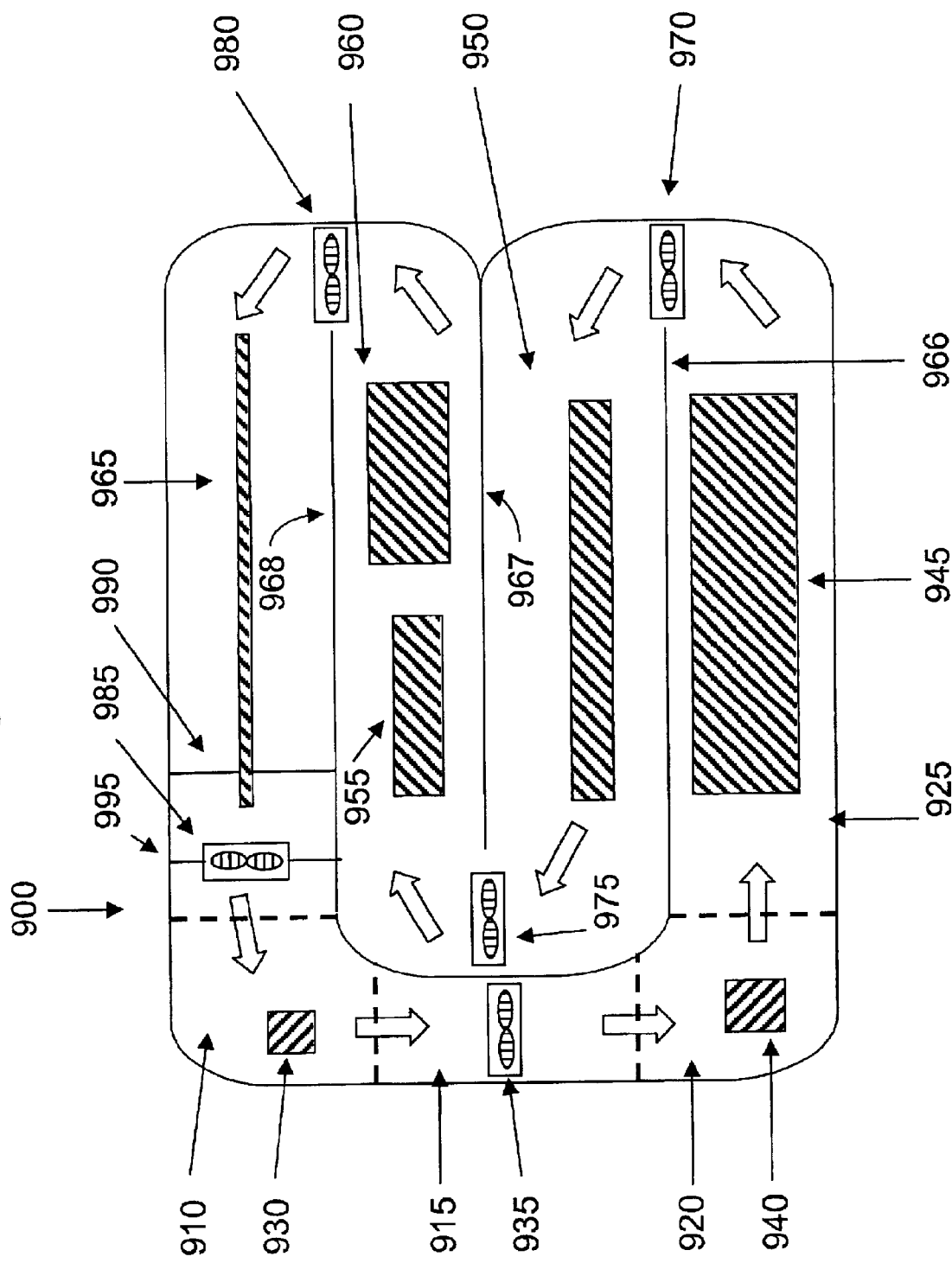
FIG. 17 is a schematic view of an enclosure having additional partition within the enclosure to separate the articles to be sterilized or disinfected.

FIG. 17 shows a container 900 having compartments 910, 915, 920, and 925 with an indicator 930, a fan 935, an antimicrobial source 940, and devices 945, 950, 955, 960, and 965 to be sterilized or disinfected, respectively. All corners of the container 900 are rounded to enhance the flow of the antimicrobial agent. Dividers 966, 967, and 968 in the compartment 925 divide the area 925 into smaller areas. All the areas are in fluid communication through the circuitous path in the compartment 925. The use of dividers can enhance the efficacy for the lumen device. The dividers separate the devices, reduce the open space around the lumen device, increase the percentage of cross-sectional area of the lumen device to the open space around the lumen device, and therefore enhance the flow of the antimicrobial agent through the lumen devices to be processed. Additional fans 970, 975, 980, and 985 can also be placed in the container 900 to enhance the circulation of the antimicrobial agent from the antimicrobial source 940, through the devices 945, 950, 955, 960, and 965, the indicator 930, the fan 935, and then back to the antimicrobial source 940. Optionally, partitions 990 and 995 can be used in the compartment 925 to enhance the flow of antimicrobial agent through longer and/or smaller lumen device 965.

Figure 18A:
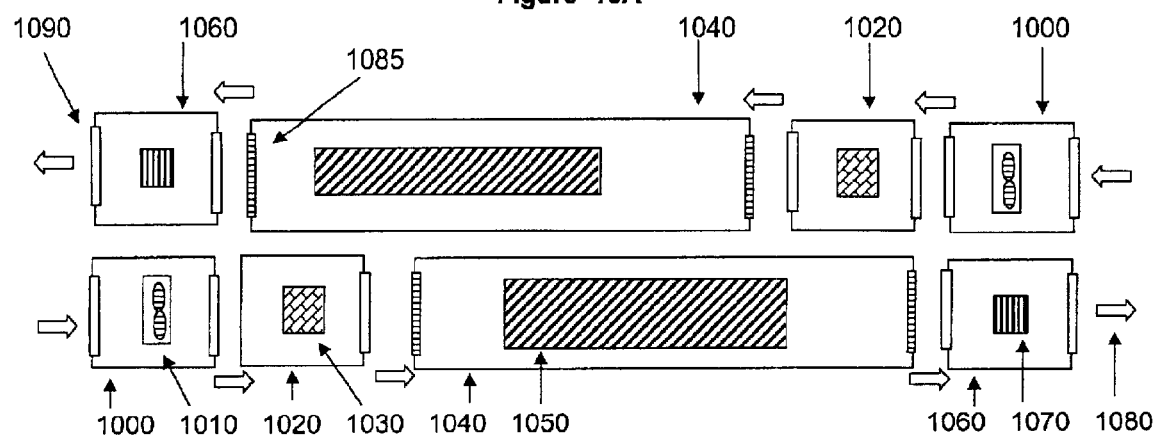
FIGS. 18A, 18B, and 18C are schematic views of attachable/detachable compartments for all components.
Figure 18B:
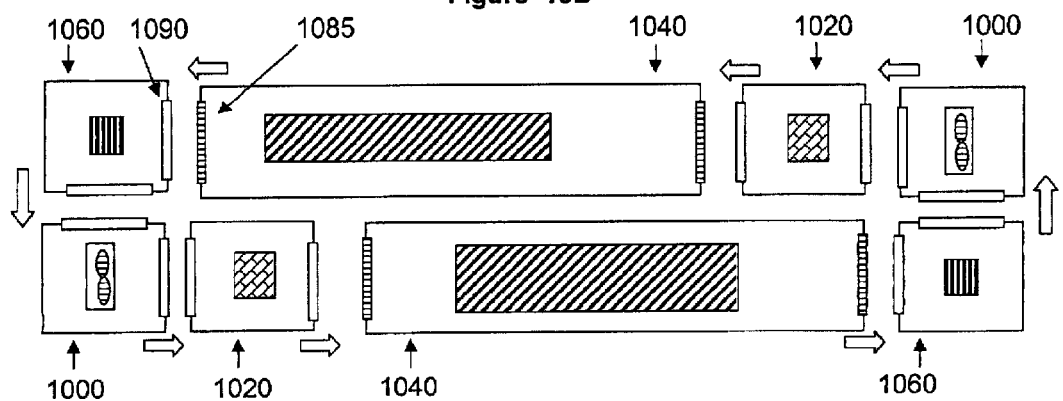
Figure 18C:
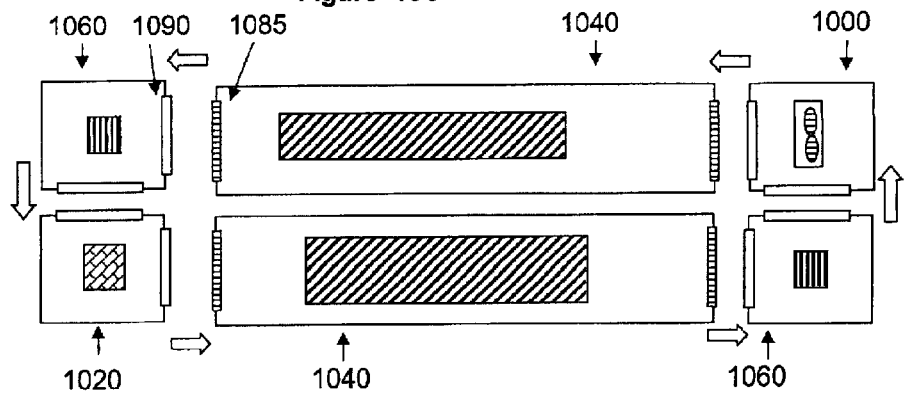

FIGS. 18A, 18B, and 18C show alternative configurations to disinfect or sterilize devices with attachable and detachable compartments. Compartment 1000 contains at least one fan 1010, compartment 1020 contains the antimicrobial agent or source of antimicrobial agent 1030, compartment 1040 contains at least one device 1050 to be sterilized or disinfected, and compartment 1060 contains at least one indicator 1070. The arrow 1080 indicates the flow of the antimicrobial agent from compartment 1020 through compartment 1040 and to compartment 1060. Compartment 1040 has gas or vapor permeable and microorganism impermeable material or barrier 1085 in order to isolate the device 1050 from microorganism when the compartments are detached. The barrier 1090 for other compartments 1000, 1020, and 1060 does not necessary to be microorganism impermeable barrier. It can be either microorganism permeable or impermeable barrier. FIG. 18A shows two sets of independent attachable and detachable compartments. Each set has its own fan 1010, source of antimicrobial agent 1030, device 1050 to be processed, and indicator 1070. FIG. 18B shows a system with two sets of compartments are attached together such that the antimicrobial agent can be circulated within the system. FIG. 18C shows a system with one compartment 1000 with fan, one compartment 1020 with source of antimicrobial agent, two compartments 1060 with indicators and two compartments 1040 with devices. A system with such attachable and detachable compartments can have many different combinations as long as the antimicrobial agent can flow from the source of antimicrobial agent to the device to be sterilized or disinfected, and then to the indicator. More than one compartment with the same content can be attached together. For example, two compartments 1020 containing the source of antimicrobial can be attached to each other to produce more antimicrobial agent to circulate in the system. Also, two device compartments 1040 can be attached together; therefore, more devices can be sterilized or disinfected at the same time. Each compartment may have multiple windows covered with the appropriate barrier. Each window may be equipped with a shutter to close the unnecessary openings, or the barrier can also be replaced with an end plate to ensure the flow of the antimicrobial agent through the right directions. A heating element can be incorporated into one or more of the attachable and detachable compartments, it can also placed in a separated attachable and detachable compartment. The heating element can also be a heating oven. Valves can also be used to isolate the compartments.

FIG. 19 shows a pouch 1100 made of gas or vapor impermeable material having a gas or vapor permeable and microorganism impermeable window 1105 for diffusing the antimicrobial agent from outside of the pouch to inside of the pouch. The pouch 1100 has an opening 1110 for placing the device 1115 into the pouch, at least one indicator 1120 for indicating the sterilization or disinfection process, and peelable heat seals 1125 for sealing the pouch and separating the indicator 1120 from the device 1115 in the pouch. The indicator 1120 is sandwiched between two gas or vapor impermeable barriers, therefore, the antimicrobial agent cannot diffuse from outside of the pouch 1100 directly into the area 1130 containing the indicator 1120. The indicator 1120 can be a chemical indicator and/or a biological indicator. Preferably, the area 1130 contains one chemical indicator and one biological indicator. The chemical indicator 1120 can be a substrate printed with chemical indicator. The chemical indicator can also be printed directly on the inner layer of the pouch 1100. The biological indicator can be a packaged strip contaminated with test microorganisms or a self-contained biological indicator. The area 1130 is in fluid communication with the area 1135 through the opening 1140 between the heat seals. The antimicrobial agent needs to diffuse into the area 1135 of the pouch 1100 through the window 1105 before it can diffuse into the area 1130. Therefore, the device 1115 in the area 1135 contacts the antimicrobial agent before the indicator 1120 in the area 1130 contacts the antimicrobial agent. The area 1135 can have more than one gas or vapor permeable and microorganism impermeable window, and the windows can be located on either one side of the pouch or both sides of the pouch. At the end of the sterilization or disinfection process, an additional heat seal can be applied to the area 1145 to completely separate the area 1130 from the area 1135, such that the indicator 1120 can be removed from the pouch 1100 without the risk of contaminating the device 1115 in the area 1135. Preferably, there is more than one indicator in the area 1130. Therefore, at the end of the process, at least one indicator can be removed from the area 1130 and still leaves at least one indicator in the area 1130 to indicate the status of the device 1115 in the pouch 1100.

FIG. 20 shows an alternative pouch 1200 similar to the pouch 1100 of FIG. 19. Pouch 1200 has multiple communication ports 1210 between the area 1220 containing the indicator 1230 and the area 1240 containing the device 1250 to be processed. Pouch 1200 also has a larger oval shape of gas or vapor permeable and microorganism impermeable window 1260 than the window 1105 on the pouch 1100 of FIG. 19. The size and shape of the gas or vapor permeable window is not critical, as long as the device 1250 in the area 1240 contacts or exposes to the antimicrobial agent before the indicator 1230 in the area 1220 contacts the antimicrobial agent.

FIG. 21 shows another alternative pouch 1300 similar to the pouch 1100 of FIG. 19. The pouch 1300 has a communication port 1310 between the area 1320 having the indicator 1330 and the area 1340 having the device 1350 to be sterilized or disinfected. The communication port is created with two partially overlapped heat seals. Pouch 1300 has a gas or vapor permeable and microorganism impermeable window 1360 for diffusing the antimicrobial agent into the pouch 1300, and the size of the window is about one side of the pouch which covers the area 1340.

Figure 22:
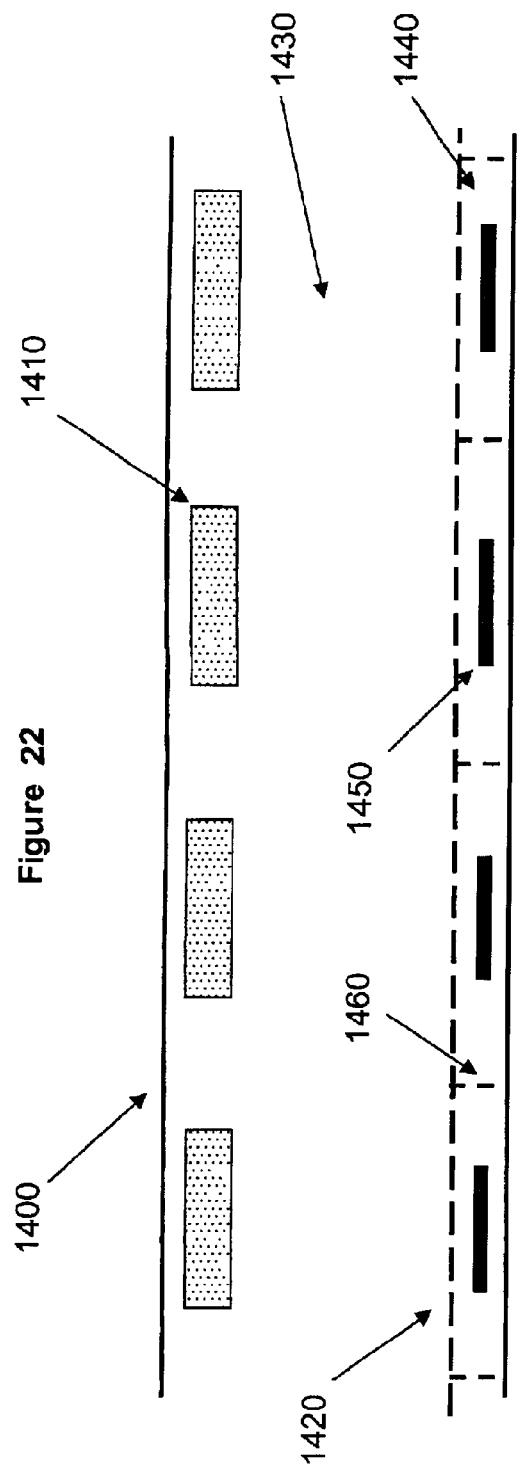
FIG. 22 is a schematic view of a section of a role of pouch having gas or vapor permeable windows and indicators separated with a partition.
Figure 23:
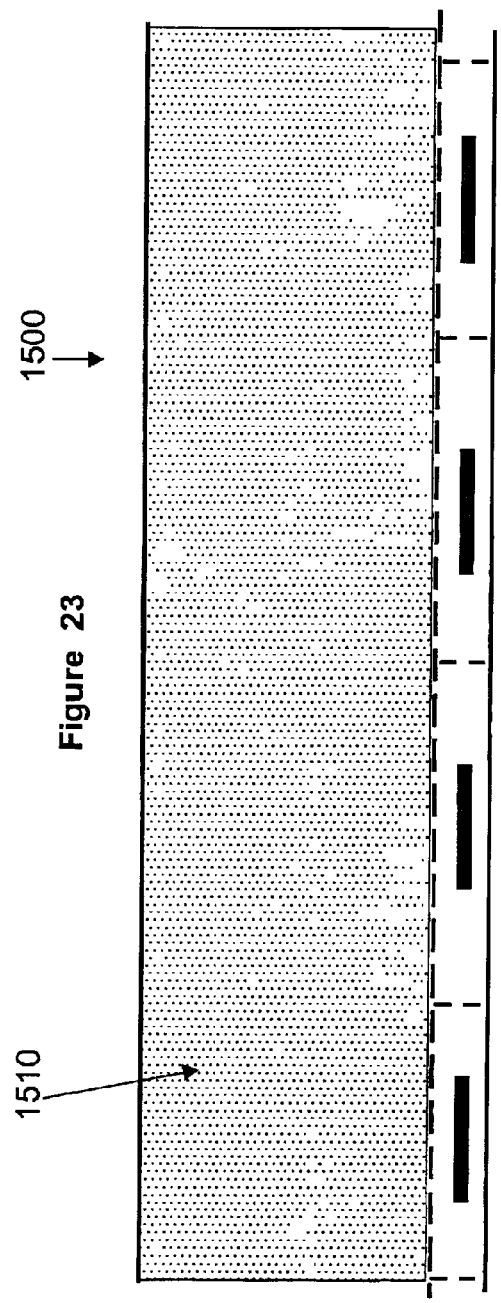
FIG. 23 is a schematic view of another alternative embodiment of the pouch.

FIG. 22 shows a section of pouch 1400 of a roll of pouch. The pouch 1400 is made of gas or vapor impermeable material with gas or vapor permeable and microorganism impermeable window 1410 for diffusing the antimicrobial agent into the pouch 1400. A heat-sealed partition 1420 separates the pouch 1400 into areas 1430 and 1440. Areas 1430 and 1440 are in fluid communication through openings between heat seals. Area 1430 contains the device to be sterilized or disinfected, and area 1440 contains the indicator 1450. The indicator can be chemical indicator and/or biological indicator. An optional partition 1460 can be used to separate the indicators in the pouch 1400. Preferably, the indicator is the chemical indicator printed on the inner layer of the pouch. During the actual use, the user cuts an appropriate section of pouch from the roll of the pouch, places the device into the pouch, and then heat-seals the open ends of the pouch. The antimicrobial agent can diffuse from the outside of the pouch 1400 through the window 1410 into the area 1430, and then diffuse from area 1430 through the partition 1420 into the area 1440. The antimicrobial agent diffuses and contacts the device in the area 1430 before it diffuses and contacts the indicator 1450 in the area 1440. FIG. 23 shows a section of pouch 1500 similar to the pouch 1400 of FIG. 22 but with a larger gas or vapor permeable and microorganism impermeable window 1510. The use of this pouch 1500 and the placements of the indicator and devices are the same as the pouch 1400 described in the FIG. 22.

It will be appreciated that, in all above embodiments, upon completion of the disinfection or sterilization cycle the process monitor cartridge can be advantageously removed from system to determine chemical and biological efficacy of the sterilization process. As opposed to prior art systems, however, the removal of the biological and chemical indicators does not disturb the sterilized state of the articles inside the sterilization container. Since the gas permeable layer only allows the passage of the steriliant vapor, removal of the cartridge from the sterilizing container will not break the sealed status of the container.

Hence, although the foregoing description of the preferred embodiment of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should not be limited to the foregoing discussions, but should be defined by the appended claims.

What is claimed is:

1. A system for monitoring a sterilization or disinfection process comprising:

a container defining a first space and a second space, the first space and second spac being in fluid communication with each other;

the first space being adapted to contain one or more articles to be sterilized or disinfected;

the second space having therein at least one indicator for indicating at least one parameter relevant to the sterilization or disinfection process;

an antimicrobial source for providing an antimicrobial agent to the first space, wherein the antimicrobial source comprises an aperture into the first space from outside of the container whereby antimicrobial fluids in space around the container may diffuse into the first space through the aperture, a flow restriction between the first space and the second space; and wherein the second space is in fluid communication with the antimicrobial source only through the first space.

2. A system according to claim 1 wherein the container is impermeable to microorganisms.

3. A system according to claim 1 wherein the second space is detachable from the first space.

4. A system according to claim 1 wherein the container comprises a pouch.

5. A system according to claim 1 wherein the indicator comprises a biological indicator.

6. A system according to claim 1 wherein the indicator comprises a chemical indicator.

7. A system according to claim 6 wherein the container comprises a pouch and wherein the chemical indicator is printed on the pouch inside the second space.

8. A system according to claim 1 and further comprising a flow restriction between the first space and the second space.

9. A system according to claim 1 wherein the first space is divided into two or more subspaces connected in series between the source of antimicrobial fluid and the second space.

10. A system according to claim 1 wherein the antimicrobial fluid comprises hydrogen peroxide.

11. A system according to claim 1 and further comprising a fan adapted to assist flow through the container from the source of antimicrobial fluid to the second space.

12. A system for monitoring a sterilization or disinfection process comprising:

a container defining a first space and a second space, the first space and second space being in fluid communication with each other;

the first space being adapted to contain one or more articles to be sterilized or disinfected;

the second space having therein at least one indicator for indicating at least one parameter relevant to the sterilization or disinfection process;

a flow restriction between the first space and the second space;

an antimicrobial source for providing an antimicrobial agent to the first space; and wherein the second space is in fluid communication with the antimicrobial source only through the first space.

13. A system for monitoring a sterilization or disinfection process comprising:

a container defining a first space and a second space, the first space and second space being in fluid communication with each other;

the first space being adapted to contain one or more articles to be sterilized or disinfected;

the second space having therein at least one indicator for indicating at least one parameter relevant to the sterilization or disinfection process;

the first space being divided into two or more subspaces connected in series between the source of antimicrobial fluid and the second space;

an antimicrobial source for providing an antimicrobial agent to the first space; and wherein the second space is in fluid communication with the antimicrobial source only through the first space.

14. A system according to claim 13 wherein at least a portion of the subspaces are detachable from the container.

15. A system for monitoring a sterilization or disinfection process comprising:

a container defining a first space and a second space, the first space and second space being in fluid communication with each other;

the first space being adapted to contain one or more articles to be sterilized or disinfected;

the second space having therein at least one indicator for indicating at least one parameter relevant to the sterilization or disinfection process;

an antimicrobial source for providing an antimicrobial agent to the first space wherein the antimicrobial fluid comprises hydrogen peroxide; and wherein the second space is in fluid communication with the antimicrobial source only through the first space.

16. A system for monitoring a sterilization or disinfection process comprising:

a container defining a first space and a second space, the first space and second space being in fluid communication with each other;

the first space being adapted to contain one or more articles to be sterilized or disinfected;

the second space having therein at least one indicator for indicating at least one parameter relevant to the sterilization or disinfection process;

an antimicrobial source for providing an antimicrobial agent to the first space;

wherein the second space is in fluid communication with the antimicrobial source only through the first space; and further comprising a fan adapted to assist flow through the container from the source of antimicrobial fluid to the second space.

17. A method for monitoring a disinfection or sterilization procedure comprising the steps of:

providing a container having a first space and a second space in fluid communication with each other;

placing an article to be disinfected or sterilized into the first space;

placing at least one indicator into the second space;

providing an antimicrobial agent to the first space;

flowing said antimicrobial agent to the second space only from the first space and reading a relevant function of the disinfection or sterilization procedure with the indicator; and wherein the antimicrobial agent comprises hydrogen peroxide.

18. A method according to claim 19 wherein the antimicrobial agent comprises hydrogen peroxide vapor.

19. A method for monitoring a disinfection or sterilization procedure comprising the steps of:

providing a container having a first space and a second space in fluid communication with each other;

placing an article to be disinfected or sterilized into the first space;

placing at least one indicator into the second space;

providing an antimicrobial agent to the first space;

flowing said antimicrobial agent to the second space only from the first space and reading a relevant function of the disinfection or sterilization procedure with the indicator; and further comprising the step of assisting the flow of the antimicrobial agent through the first space and to the second space with a fan.

20. A method for monitoring a disinfection or sterilization procedure comprising the steps of:

providing a container having a first space and a second space in fluid communication with each other;

placing an article to be disinfected or sterilized into the first space;

placing at least one indicator into the second space;

providing an antimicrobial agent to the first space;

flowing said antimicrobial agent to the second space only from the first space and reading a relevant function of the disinfection or sterilization procedure with the indicator; and further comprising the step of recirculating the antimicrobial agent back to the first space from the second space.

21. A method for monitoring a disinfection or sterilization procedure comprising the steps of:

providing a container having a first space and a second space in fluid communication with each other;

placing an article to be disinfected or sterilized into the first space;

placing at least one indicator into the second space;

providing an antimicrobial agent to the first space;

flowing said antimicrobial agent to the second space only from the first space and reading a relevant function of the disinfection or sterilization procedure with the indicator; and wherein the container is a pouch and further comprising the step of sealing the first space from the second space after flowing the antimicrobial agent into the second space and then removing the indicator from the second space.

22. A method according to claim 21 wherein the step of sealing the first space from the second space comprises heat sealing a portion of the pouch between the first space and the second space.

* * * * *